United States Patent
McCarthy et al.

(10) Patent No.: US 12,049,519 B2
(45) Date of Patent: Jul. 30, 2024

(54) PEPTIDE FOR THE DELIVERY OF ANIONIC MATERIALS

(71) Applicant: The Queen's University of Belfast, Belfast (GB)

(72) Inventors: Helen McCarthy, Belfast (GB); Nicholas Dunne, Belfast (GB); Tracy Robson, Belfast (GB); Emma McErlean, Belfast (GB); Eoghan Mulholland, Belfast (GB); Grace Cole, Belfast (GB)

(73) Assignee: The Queen's University of Belfast, Belfast (GB)

( * ) Notice: Subject to any disclaimer, the term of this patent is extended or adjusted under 35 U.S.C. 154(b) by 407 days.

(21) Appl. No.: 17/437,025

(22) PCT Filed: Mar. 9, 2020

(86) PCT No.: PCT/EP2020/056216
§ 371 (c)(1),
(2) Date: Sep. 7, 2021

(87) PCT Pub. No.: WO2020/182728
PCT Pub. Date: Sep. 17, 2020

(65) Prior Publication Data
US 2022/0389059 A1 Dec. 8, 2022

(30) Foreign Application Priority Data

Mar. 8, 2019 (GB) .................................. 1903132

(51) Int. Cl.
*C07K 7/08* (2006.01)
*A61P 35/00* (2006.01)
*C12N 15/87* (2006.01)
(52) U.S. Cl.
CPC ............... *C07K 7/08* (2013.01); *A61P 35/00* (2018.01); *C12N 15/87* (2013.01); *C07K 2318/20* (2013.01)

(58) Field of Classification Search
CPC ....... C07K 7/08; C07K 2318/20; A61P 35/00; C12N 15/87
See application file for complete search history.

(56) References Cited

FOREIGN PATENT DOCUMENTS

| CN | 106800592 A | 6/2017 |
|---|---|---|
| WO | 2014/072999 A1 | 5/2014 |

OTHER PUBLICATIONS

Mann, A., et al., Linear Short Histidine and Cysteine Modified Arginine Peptides Constitute a Potential Class of DNA Delivery Agents, Molecular Pharmaceutics, Jan. 29, 2014, vol. 11, No. 3, pp. 683-696.

Rydberg, H.A., et al., Effects of Tryptophan Content and Backbone Spacing on Uptake Efficiency of Cell-Penetrating Peptides, Biophysical Journal, Feb. 28, 2012, vol. 102, No. 3, 1 page.

Wolfe, J.M., et al., Machine Learning To Predict Cell-Penetrating Peptides for Antisense Delivery, ACS Central Science, Apr. 5, 2018, vol. 4, No. 4, pp. 512-520.

*Primary Examiner* — Li N Komatsu
(74) *Attorney, Agent, or Firm* — Hodgson Russ LLP

(57) ABSTRACT

Provided is a peptide including X-(Xaa1)a-(Xaa2)b-Y-(Xaa3)c-(Xaa4)d-Z, or a salt or amide thereof, in which each of X and Z is independently selected from Asn, Cys, Gln, Gly, Ser, Thr and Tyr; in which one of Xaa1 and Xaa2 is His and the other of Xaa1 and Xaa2 is Arg; in which one of Xaa3 and Xaa4 is His and the other of Xaa3 and Xaa4 is Arg; in which the amino functional group of X is, optionally, acylated; in which the carboxylate functional group of Z is, optionally, amidated; in which Y is selected from Ala and Trp; in which each of a and d is independently an integer from 2 to 4; and each of b and c is independently an integer from 2 to 4. The peptide may be used in therapeutic approaches.

22 Claims, 23 Drawing Sheets
Specification includes a Sequence Listing.

A

NCTC-929 Fibroblast Cells

HMEC-1 Endothelial Cells

B

Figure 15:
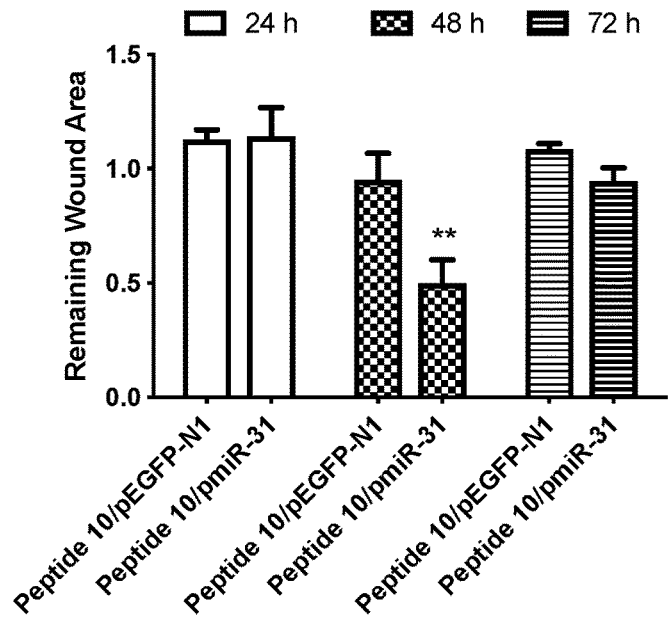
Figure 15:
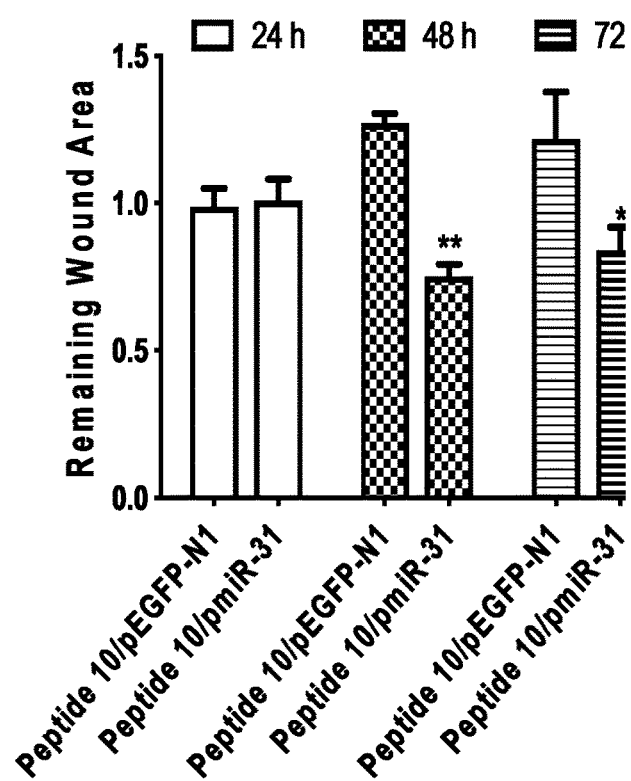

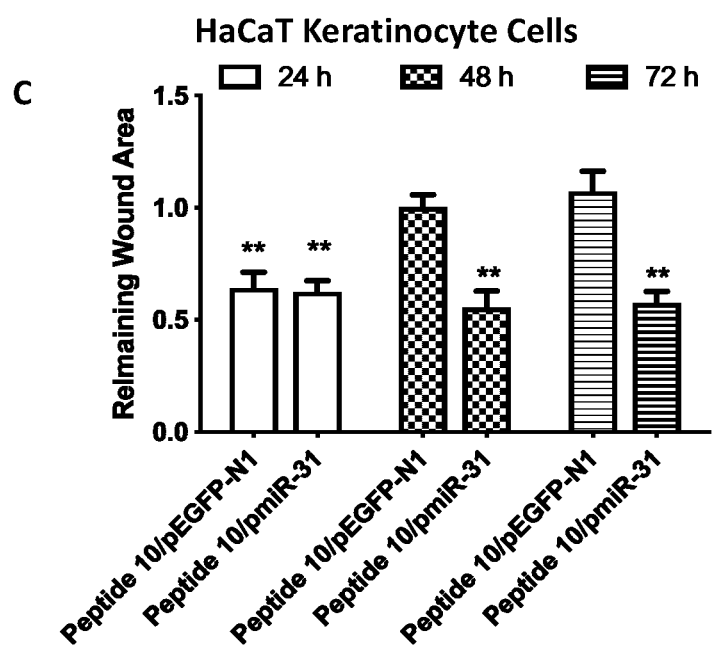
Figure 15 contd

Figure 17:
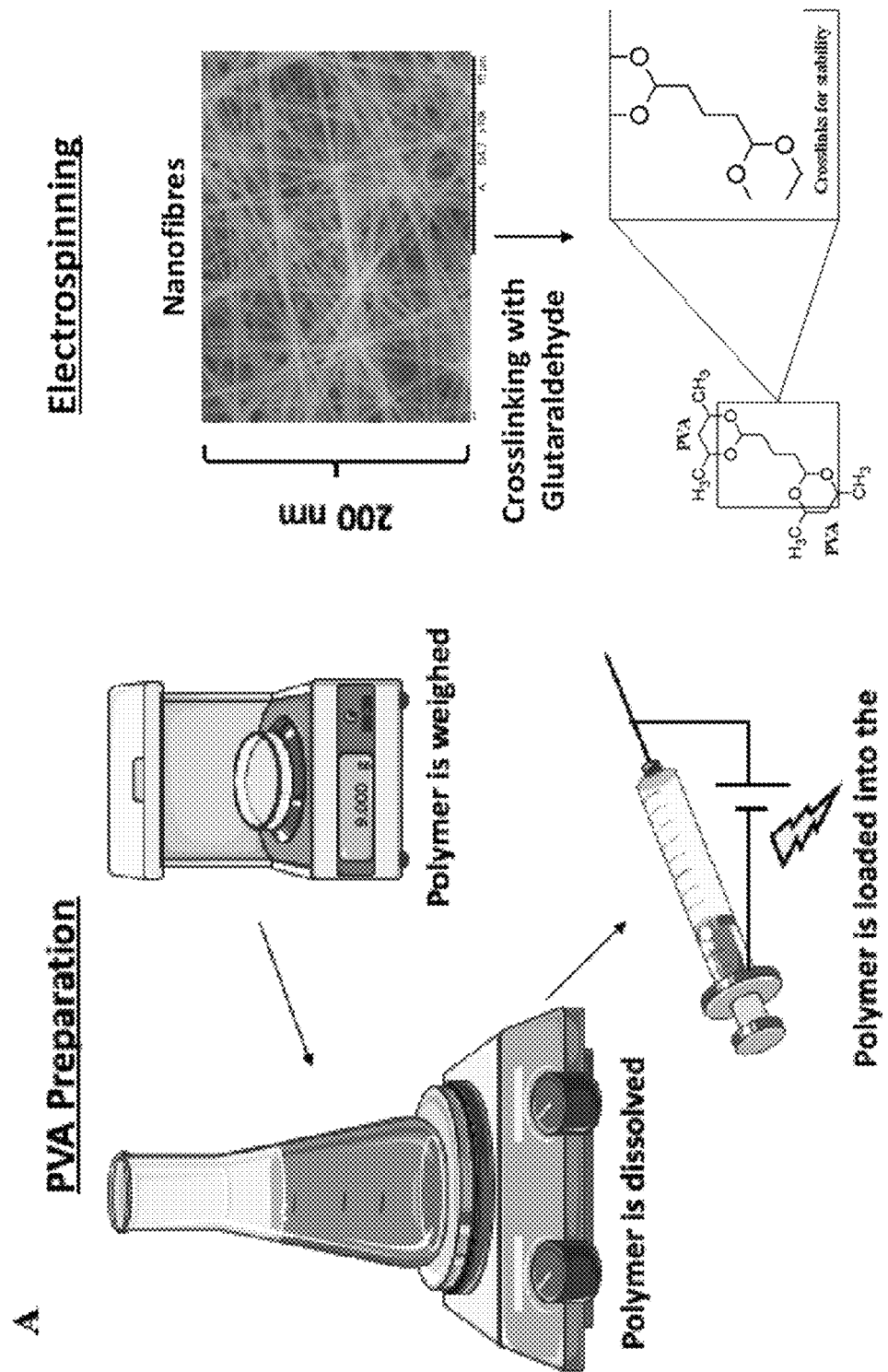

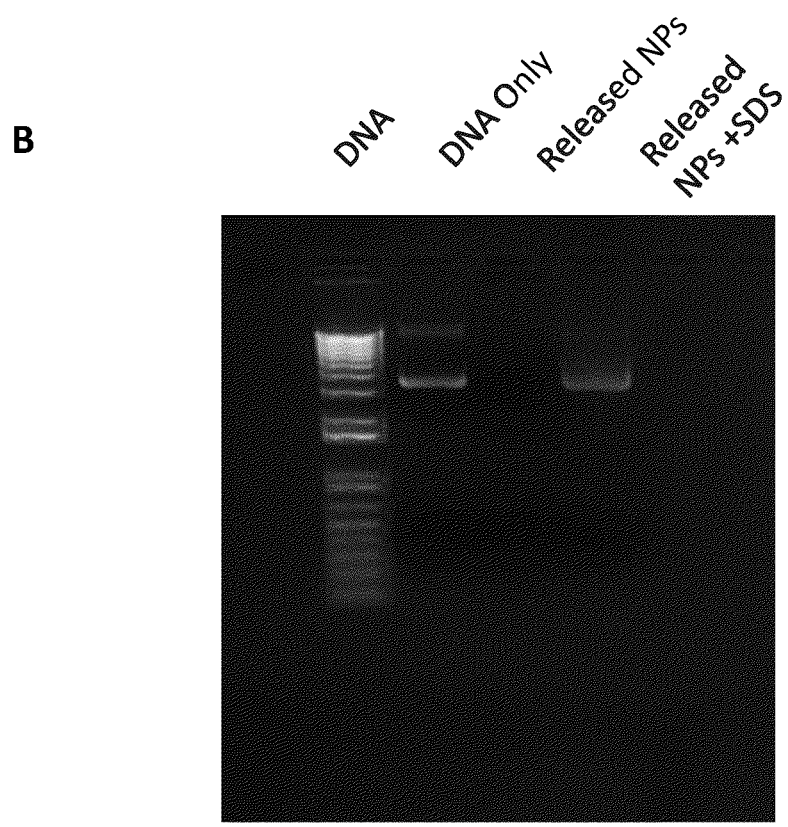
Figure 17 contd

A

B

SEQUENCE LISTING

```
<160> NUMBER OF SEQ ID NOS: 17

<210> SEQ ID NO 1
<211> LENGTH: 15
<212> TYPE: PRT
<213> ORGANISM: Unknown
<220> FEATURE:
<223> OTHER INFORMATION: Synthetic

<400> SEQUENCE: 1

Cys Arg Arg Arg Trp His His His His His Trp Arg Arg Arg Cys
1               5                   10                  15

<210> SEQ ID NO 2
<211> LENGTH: 15
<212> TYPE: PRT
<213> ORGANISM: Unknown
<220> FEATURE:
<223> OTHER INFORMATION: Synthetic

<400> SEQUENCE: 2

Cys Trp Arg Arg Arg His His His His His Arg Arg Arg Trp Cys
1               5                   10                  15

<210> SEQ ID NO 3
<211> LENGTH: 15
<212> TYPE: PRT
```

```
<213> ORGANISM: Unknown
<220> FEATURE:
<223> OTHER INFORMATION: Synthetic

<400> SEQUENCE: 3

Cys His Arg His Arg His Arg Trp His Arg His Arg His Arg Cys
1               5                   10                  15

<210> SEQ ID NO 4
<211> LENGTH: 15
<212> TYPE: PRT
<213> ORGANISM: Unknown
<220> FEATURE:
<223> OTHER INFORMATION: Synthetic

<400> SEQUENCE: 4

Cys His His His Arg Arg Arg Trp Arg Arg Arg His His His Cys
1               5                   10                  15

<210> SEQ ID NO 5
<211> LENGTH: 11
<212> TYPE: PRT
<213> ORGANISM: Unknown
<220> FEATURE:
<223> OTHER INFORMATION: Synthetic

<400> SEQUENCE: 5

Cys Arg Arg Arg Arg Trp Arg Arg Arg Arg Cys
1               5                   10

<210> SEQ ID NO 6
<211> LENGTH: 15
<212> TYPE: PRT
<213> ORGANISM: Unknown
<220> FEATURE:
<223> OTHER INFORMATION: Synthetic

<400> SEQUENCE: 6

Cys Glu His His Arg Arg Arg Trp Arg Arg Arg His His Glu Cys
1               5                   10                  15

<210> SEQ ID NO 7
<211> LENGTH: 8
<212> TYPE: PRT
<213> ORGANISM: Unknown
<220> FEATURE:
<223> OTHER INFORMATION: Synthetic

<400> SEQUENCE: 7

Arg Arg Arg Arg Arg Arg Arg Arg
1               5

<210> SEQ ID NO 8
<211> LENGTH: 11
<212> TYPE: PRT
<213> ORGANISM: Unknown
<220> FEATURE:
<223> OTHER INFORMATION: Synthetic

<400> SEQUENCE: 8

Tyr Gly Arg Lys Lys Arg Arg Gln Arg Arg Arg
1               5                   10

<210> SEQ ID NO 9
<211> LENGTH: 9
<212> TYPE: PRT
<213> ORGANISM: Unknown
```

```
<220> FEATURE:
<223> OTHER INFORMATION: Synthetic

<400> SEQUENCE: 9

Arg Arg Arg Arg Arg Arg Arg Arg
1               5

<210> SEQ ID NO 10
<211> LENGTH: 22
<212> TYPE: PRT
<213> ORGANISM: Unknown
<220> FEATURE:
<223> OTHER INFORMATION: Synthetic

<400> SEQUENCE: 10

Cys His His His His His Arg Lys Lys Arg Arg Gln Arg Arg Arg
1               5                   10                  15

His His His His His Cys
            20

<210> SEQ ID NO 11
<211> LENGTH: 21
<212> TYPE: PRT
<213> ORGANISM: Unknown
<220> FEATURE:
<223> OTHER INFORMATION: Synthetic

<400> SEQUENCE: 11

His His His His His Tyr Gly Arg Lys Lys Arg Arg Gln Arg Arg
1               5                   10                  15

His His His His His
            20

<210> SEQ ID NO 12
<211> LENGTH: 5936
<212> TYPE: DNA
<213> ORGANISM: Unknown
<220> FEATURE:
<223> OTHER INFORMATION: Synthetic

<400> SEQUENCE: 12
gcgatcgcgg ctcccgacat cttggaccat tagctccaca ggtatcttct tccctctagt      60
ggtcataaca gcagcttcag ctacctctca attcaaaaaa cccctcaaga cccgtttaga     120
ggccccaagg ggttatgcta tcaatcgttg cgttacacac acaaaaaacc aacacacatc     180
catcttcgat ggatagcgat tttattatct aactgctgat cgagtgtagc cagatctagt     240
aatcaattac ggggtcatta gttcatagcc catatatgga gttccgcgtt acataactta     300
cggtaaatgg cccgcctggc tgaccgccca acgaccccg cccattgacg tcaataatga      360
cgtatgttcc catagtaacg ccaataggga ctttccattg acgtcaatgg gtggagtatt     420
tacggtaaac tgcccacttg gcagtacatc aagtgtatca tatgccaagt acgcccccta     480
ttgacgtcaa tgacggtaaa tggcccgcct ggcattatgc ccagtacatg accttatggg     540
actttcctac ttggcagtac atctacgtat tagtcatcgc tattaccatg ctgatgcggt     600
tttggcagta catcaatggg cgtggatagc ggtttgactc acggggattt ccaagtctcc     660
accccattga cgtcaatggg agtttgtttt ggcaccaaaa tcaacgggac tttccaaaat     720
gtcgtaacaa ctccgcccca ttgacgcaaa tgggcggtag cgtgtacgg tgggaggtct      780
atataagcag agctggttta gtgaaccgtc agatcagatc tttgtcgatc ctaccatcca     840
ctcgacacac ccgccagcgg ccgctgccaa gcttccgagc tctcgaattc aaaggaggta     900
```

```
cccaccatgg aagatgccaa aaacattaag aaaggcccag cgccattcta cccactcgaa    960
gacgggaccg ctggcgagca gctgcataaa gccatgaagc gctacgccct ggtgccaggc   1020
accatcgcct taccgacgc acatatcgag gtggacatta cctacgccga gtacttcgag   1080
atgagcgttc ggctggcaga agctatgaag cgctatgggc tgaatacaaa ccatcggatc   1140
gtggtgtgta gcgagaatag cttgcagttc ttcatgcccg tgttgggtgc cctgttcatc   1200
ggtgtggctg tggccccagc taacgacatc tacaacgagc gcgagctgct gaacagcatg   1260
ggcatcagcc agcccaccgt cgtattcgtg agcaagaaag ggctgcaaaa gatcctcaac   1320
gtgcaaaaga agctaccgat catacaaaag atcatcatca tggatagcaa gaccgactac   1380
cagggcttcc aaagcatgta caccttcgtg acttcccatt tgccacccgg cttcaacgag   1440
tacgacttcg tgcccgagag cttcgaccgg gacaaaacca tcgccctgat catgaacagt   1500
agtggcagta ccggattgcc caagggcgta gccctaccgc accgcaccgc ttgtgtccga   1560
ttcagtcatg cccgcgaccc catcttcggc aaccagatca tccccgacac cgctatcctg   1620
agcgtggtgc catttcacca cggcttcggc atgttcacca cgctgggcta cttgatctgc   1680
ggctttcggg tcgtgctcat gtaccgcttc gaggaagagc tattcttgcg cagcttgcaa   1740
gactataaga ttcaatctgc cctgctggtg cccacactat ttagcttctt cgctaagagc   1800
actctcatcg acaagtacga cctaagcaac ttgcacgaga tcgccagcgg cggggcgccg   1860
ctcagcaagg aggtaggtga ggccgtggcc aaacgcttcc acctaccagg catccgccag   1920
ggctacggcc tgacagaaac aaccagcgcc attctgatca cccccgaagg ggacgacaag   1980
cctggcgcag taggcaaggt ggtgcccttc ttcgaggcta aggtggtgga cttggacacc   2040
ggtaagacac tgggtgtgaa ccagcgcggc gagctgtgcg tccgtggccc catgatcatg   2100
agcggctacg ttaacaaccc cgaggctaca aacgctctca tcgacaagga cggctggctg   2160
catagcggcg acatcgccta ctgggacgag gacgagcact tcttcatcgt ggaccggctg   2220
aagagcctga tcaaatacaa gggctaccag gtagccccag ccgaactgga gagcatcctg   2280
ctgcaacacc ccaacatctt cgacgccggg gtcgccggcc tgcccgacga cgatgccggc   2340
gagctgcccg ccgcagtcgt cgtgctggaa cacggtaaaa ccatgaccga aggagatc    2400
gtggactatg tggccagcca ggttacaacc gccaagaagc tgcgcggtgg tgttgtgttc   2460
gtggacgagt gcctaaaggg actgaccggc aagttggacg cccgcaagat ccgcgagatt   2520
ctcattaagg ccaagaaggg cggcaagatc gccgtctaga agttgtctcc tcctgcactg   2580
actgactgat acaatcgatt tctggatccg caggcctctg ctagcttgac tgactgagat   2640
acagcgtacc ttcagctcac agacatgata agatacattg atgagtttgg acaaaccaca   2700
actagaatgc agtgaaaaaa atgctttatt tgtgaaattt gtgatgctat tgctttattt   2760
gtaaccatta taagctgcaa taaacaagtt aacaacaaca attgcattca ttttatgttt   2820
caggttcagg gggaggtgtg ggaggttttt taaagcaagt aaaacctcta caaatgtggt   2880
attggcccat ctctatcggt atcgtagcat aaccccttgg ggcctctaaa cgggtcttga   2940
ggggttttt gtgcccctcg gccggattg ctatctaccg gcattggcgc agaaaaaaat   3000
gcctgatgcg acgctgcgcg tcttatactc ccacatatgc cagattcagc aacggatacg   3060
gcttccccaa cttgcccact tccatacgtg tcctccttac cagaaattta tccttaaggt   3120
cgtcagctat cctgcaggcg atctctcgat ttcgatcaag acattccttt aatggtcttt   3180
tctggacacc actaggggtc agaagtagtt catcaaactt tcttccctcc ctaatctcat   3240
```

```
tggttacctt gggctatcga acttaatta accagtcaag tcagctactt ggcgagatcg   3300
acttgtctgg gtttcgacta cgctcagaat tgcgtcagtc aagttcgatc tggtccttgc   3360
tattgcaccc gttctccgat tacgagtttc atttaaatca tgtgagcaaa aggccagcaa   3420
aaggccagga accgtaaaaa ggccgcgttg ctggcgtttt tccataggct ccgcccccct   3480
gacgagcatc acaaaaatcg acgctcaagt cagaggtggc gaaacccgac aggactataa   3540
agataccagg cgtttccccc tggaagctcc ctcgtgcgct ctcctgttcc gaccctgccg   3600
cttaccggat acctgtccgc ctttctccct tcgggaagcg tggcgctttc tcatagctca   3660
cgctgtaggt atctcagttc ggtgtaggtc gttcgctcca agctgggctg tgtgcacgaa   3720
ccccccgttc agcccgaccg ctgcgcctta tccggtaact atcgtcttga gtccaacccg   3780
gtaagacacg acttatcgcc actggcagca gccactggta acaggattag cagagcgagg   3840
tatgtaggcg gtgctacaga gttcttgaag tggtggccta actacggcta cactagaaga   3900
acagtatttg gtatctgcgc tctgctgaag ccagttacct tcggaaaaag agttggtagc   3960
tcttgatccg gcaaacaaac caccgctggt agcggtggtt tttttgtttg caagcagcag   4020
attacgcgca gaaaaaaagg atctcaagaa gatcctttga tcttttctac ggggtctgac   4080
gctcagtgga acgaaaactc acgttaaggg attttggtca tgagattatc aaaaaggatc   4140
ttcacctaga tccttttaaa ttaaaaatga agttttaaat caatctaaag tatatatgag   4200
taaacttggt ctgacagtta ccaatgctta atcagtgagg cacctatctc agcgatctgt   4260
ctatttcgtt catccatagt tgcatttaaa tttccgaact ctccaaggcc ctcgtcggaa   4320
aatcttcaaa cctttcgtcc gatccatctt gcaggctacc tctcgaacga actatcgcaa   4380
gtctcttggc cggccttgcg ccttggctat tgcttggcag cgcctatcgc caggtattac   4440
tccaatcccg aatatccgag atcgggatca cccgagagaa gttcaaccta catcctcaat   4500
cccgatctat ccgagatccg aggaatatcg aaatcggggc gcgcctggtg taccgagaac   4560
gatcctctca gtgcgagtct cgacgatcca tatcgttgct tggcagtcag ccagtcggaa   4620
tccagcttgg gacccaggaa gtccaatcgt cagatattgt actcaagcct ggtcacggca   4680
gcgtaccgat ctgtttaaac ctagatattg atagtctgat cggtcaacgt ataatcgagt   4740
cctagctttt gcaaacatct atcaagagac aggatcagca ggaggctttc gcatgagtat   4800
tcaacatttc cgtgtcgccc ttattcccct ttttgcggca ttttgccttc ctgtttttgc   4860
tcacccagaa acgctggtga agtaaaaga tgctgaagat cagttgggtg cgcgagtggg   4920
ttacatcgaa ctggatctca acagcggtaa gatccttgag agttttcgcc ccgaagaacg   4980 cttttccaatg atgagcactt ttaaagttct gctatgtggc gcggtattat cccgtattga   5040
cgccgggcaa gagcaactcg gtcgccgcat acactattct cagaatgact tggttgagta   5100
ttcaccagtc acagaaaagc atcttacgga tggcatgaca gtaagagaat tatgcagtgc   5160
tgccataacc atgagtgata acactgcggc caacttactt ctgacaacga ttggaggacc   5220
gaaggagcta accgcttttt tgcacaacat ggggatcat gtaactcgcc ttgatcgttg   5280
ggaaccggag ctgaatgaag ccataccaaa cgacgagcgt gacaccacga tgcctgtagc   5340
aatggcaaca accttgcgta actattaac tggcgaacta cttactctag cttcccggca   5400
acagttgata gactggatgg aggcggataa agttgcagga ccacttctgc gctcggccct   5460
tccggctggc tggtttattg ctgataaatc tggagccggt gagcgtgggt ctcgcggtat   5520
cattgcagca ctggggccag atggtaagcc ctcccgtatc gtagttatct acacgacggg   5580
gagtcaggca actatggatg aacgaaatag acagatcgct gagataggtg cctcactgat   5640
```

```
taagcattgg taaccgattc taggtgcatt ggcgcagaaa aaaatgcctg atgcgacgct    5700
gcgcgtctta tactcccaca tatgccagat tcagcaacgg atacggcttc cccaacttgc    5760
ccacttccat acgtgtcctc cttaccagaa atttatcctt aagatcccga atcgtttaaa    5820
ctcgactctg gctctatcga atctccgtcg tttcgagctt acgcgaacag ccgtggcgct    5880
catttgctcg tcgggcatcg aatctcgtca gctatcgtca gcttaccttt ttggca       5936
```

```
<210> SEQ ID NO 13
<211> LENGTH: 19
<212> TYPE: PRT
<213> ORGANISM: Unknown
<220> FEATURE:
<223> OTHER INFORMATION: Synthetic
<220> FEATURE:
<221> NAME/KEY: VARIANT
<222> LOCATION: (1)..(1)
<223> OTHER INFORMATION: X is Asn, Cys, Gln, Gly, Ser, Thr and Tyr
<220> FEATURE:
<221> NAME/KEY: VARIANT
<222> LOCATION: (1)..(19)
<223> OTHER INFORMATION: The peptide may comprise an amide derived from
      a fatty acid, for example, a stearoyl group may be tethered to the
      peptide
<220> FEATURE:
<221> NAME/KEY: VARIANT
<222> LOCATION: (1)..(1)
<223> OTHER INFORMATION: the amino functional group of X is, optionally,
      acylated
<220> FEATURE:
<221> NAME/KEY: VARIANT
<222> LOCATION: (1)..(1)
<223> OTHER INFORMATION: Optionally, X is selected from Asn, Cys, Gln,
      Gly, Ser, Thr and Tyr and is identical to Z
<220> FEATURE:
<221> NAME/KEY: VARIANT
<222> LOCATION: (1)..(19)
<223> OTHER INFORMATION: Optionally, the sum of b plus c is at least
      six, so that the peptide comprises a minimum of six Arg residues
<220> FEATURE:
<221> NAME/KEY: VARIANT
<222> LOCATION: (1)..(19)
<223> OTHER INFORMATION: Optionally, the sum of a plus d is at least
      six, so that the peptide comprises a minimum of six His residues.
<220> FEATURE:
<221> NAME/KEY: VARIANT
<222> LOCATION: (2)..(5)
<223> OTHER INFORMATION: Xaa1 is His or Arg
<220> FEATURE:
<221> NAME/KEY: VARIANT
<222> LOCATION: (2)..(6)
<223> OTHER INFORMATION: a is 2 to 4 amino acids
<220> FEATURE:
<221> NAME/KEY: VARIANT
<222> LOCATION: (2)..(6)
<223> OTHER INFORMATION: a is 2 to 4 amino acids
<220> FEATURE:
<221> NAME/KEY: VARIANT
<222> LOCATION: (6)..(9)
<223> OTHER INFORMATION: Xaa2 is His or Arg
<220> FEATURE:
<221> NAME/KEY: VARIANT
<222> LOCATION: (6)..(9)
<223> OTHER INFORMATION: b is 2 to 4 amino acids
<220> FEATURE:
<221> NAME/KEY: VARIANT
<222> LOCATION: (10)..(10)
<223> OTHER INFORMATION: when Y is Trp, the indole ring may be
      N-alkylated
<220> FEATURE:
<221> NAME/KEY: VARIANT
<222> LOCATION: (10)..(10)
<223> OTHER INFORMATION: Y is Ala or Trp
<220> FEATURE:
<221> NAME/KEY: VARIANT
```

```
<222> LOCATION: (11)..(14)
<223> OTHER INFORMATION: Xaa3 is His or Arg
<220> FEATURE:
<221> NAME/KEY: VARIANT
<222> LOCATION: (11)..(14)
<223> OTHER INFORMATION: c is 2 to 4 amino acids
<220> FEATURE:
<221> NAME/KEY: VARIANT
<222> LOCATION: (15)..(18)
<223> OTHER INFORMATION: Xaa4 is His or Arg
<220> FEATURE:
<221> NAME/KEY: VARIANT
<222> LOCATION: (15)..(18)
<223> OTHER INFORMATION: d is 2 to 4 amino acids
<220> FEATURE:
<221> NAME/KEY: VARIANT
<222> LOCATION: (15)..(18)
<223> OTHER INFORMATION: Optionally, each Xaa4 is His
<220> FEATURE:
<221> NAME/KEY: VARIANT
<222> LOCATION: (19)..(19)
<223> OTHER INFORMATION: the carboxylate functional group of Z is,
      optionally, amidated
<220> FEATURE:
<221> NAME/KEY: VARIANT
<222> LOCATION: (19)..(19)
<223> OTHER INFORMATION: Optionally, Z is selected from Asn, Cys, Gln,
      Gly, Ser, Thr and Tyr and is identical to X

<400> SEQUENCE: 13

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 14
<211> LENGTH: 19
<212> TYPE: PRT
<213> ORGANISM: Unknown
<220> FEATURE:
<223> OTHER INFORMATION: Synthetic
<220> FEATURE:
<221> NAME/KEY: VARIANT
<222> LOCATION: (1)..(1)
<223> OTHER INFORMATION: X is Cys
<220> FEATURE:
<221> NAME/KEY: VARIANT
<222> LOCATION: (2)..(5)
<223> OTHER INFORMATION: Xaa1 is His; a is independently 2 to 4
<220> FEATURE:
<221> NAME/KEY: VARIANT
<222> LOCATION: (6)..(9)
<223> OTHER INFORMATION: Xaa2 is Arg; b is independently 2 to 4
<220> FEATURE:
<221> NAME/KEY: VARIANT
<222> LOCATION: (10)..(10)
<223> OTHER INFORMATION: Y is Trp, or a salt, or amide thereof
<220> FEATURE:
<221> NAME/KEY: VARIANT
<222> LOCATION: (11)..(14)
<223> OTHER INFORMATION: Xaa3 is Arg; c is independently 2 to 4
<220> FEATURE:
<221> NAME/KEY: VARIANT
<222> LOCATION: (15)..(18)
<223> OTHER INFORMATION: Xaa4 is His; d is independently 2 to 4
<220> FEATURE:
<221> NAME/KEY: VARIANT
<222> LOCATION: (19)..(19)
<223> OTHER INFORMATION: Z is Cys

<400> SEQUENCE: 14

Xaa Xaa Xaa Xaa Xaa Xaa Xaa Xaa Xaa Xaa Xaa Xaa Xaa Xaa Xaa Xaa
1               5                   10                  15

Xaa Xaa Xaa
```

```
<210> SEQ ID NO 15
<211> LENGTH: 19
<212> TYPE: PRT
<213> ORGANISM: Unknown
<220> FEATURE:
<223> OTHER INFORMATION: Synthetic
<220> FEATURE:
<221> NAME/KEY: VARIANT
<222> LOCATION: (1)..(1)
<223> OTHER INFORMATION: X is Cys
<220> FEATURE:
<221> NAME/KEY: VARIANT
<222> LOCATION: (2)..(5)
<223> OTHER INFORMATION: Xaa1 is His and a is independently 2 to 4
<220> FEATURE:
<221> NAME/KEY: VARIANT
<222> LOCATION: (6)..(9)
<223> OTHER INFORMATION: Xaa2 is Arg and b is independently 3 or 4
<220> FEATURE:
<221> NAME/KEY: VARIANT
<222> LOCATION: (10)..(10)
<223> OTHER INFORMATION: Y is Trp, or a salt, or amide thereof
<220> FEATURE:
<221> NAME/KEY: VARIANT
<222> LOCATION: (11)..(14)
<223> OTHER INFORMATION: Xaa3 is Arg and c is independently 3 or 4
<220> FEATURE:
<221> NAME/KEY: VARIANT
<222> LOCATION: (15)..(18)
<223> OTHER INFORMATION: Xaa4 is His and d is independently 2 to 4
<220> FEATURE:
<221> NAME/KEY: VARIANT
<222> LOCATION: (19)..(19)
<223> OTHER INFORMATION: Z is Cys

<400> SEQUENCE: 15

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 16
<211> LENGTH: 19
<212> TYPE: PRT
<213> ORGANISM: Unknown
<220> FEATURE:
<223> OTHER INFORMATION: Synthetic
<220> FEATURE:
<221> NAME/KEY: VARIANT
<222> LOCATION: (1)..(1)
<223> OTHER INFORMATION: X is Cys
<220> FEATURE:
<221> NAME/KEY: VARIANT
<222> LOCATION: (2)..(5)
<223> OTHER INFORMATION: Xaa1 is His; a is independently 3 or 4
<220> FEATURE:
<221> NAME/KEY: VARIANT
<222> LOCATION: (6)..(9)
<223> OTHER INFORMATION: Xaa2 is Arg; b is independently 3 or 4
<220> FEATURE:
<221> NAME/KEY: VARIANT
<222> LOCATION: (10)..(10)
<223> OTHER INFORMATION: Y is Trp, or a salt, or amide thereof
<220> FEATURE:
<221> NAME/KEY: VARIANT
<222> LOCATION: (11)..(14)
<223> OTHER INFORMATION: Xaa3 is Arg; b is independently 3 or 4
<220> FEATURE:
<221> NAME/KEY: VARIANT
<222> LOCATION: (15)..(18)
<223> OTHER INFORMATION: Xaa4 is His; d is independently 3 or 4
<220> FEATURE:
<221> NAME/KEY: VARIANT
<222> LOCATION: (19)..(19)
<223> OTHER INFORMATION: Z is Cys
```

```
<400> SEQUENCE: 16

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 17
<211> LENGTH: 15
<212> TYPE: PRT
<213> ORGANISM: artificial sequence
<220> FEATURE:
<223> OTHER INFORMATION: synthetic peptide

<400> SEQUENCE: 17

Cys His His His Arg Arg Arg Trp Arg Arg Arg His His His Cys
1               5                   10                  15
```

PEPTIDE FOR THE DELIVERY OF ANIONIC MATERIALS

SEQUENCE LISTING

The instant application contains a Sequence Listing which has been submitted electronically in ASCII format and is hereby incorporated by reference in its entirety. Said ASCII copy, created Jul. 26, 2022, is titled "FRK_00062_ST25.txt" and is 15,478 bytes in size.

FIELD OF THE INVENTION

The present invention is directed to a peptide for the delivery of anionic materials, such as anionic therapeutic agents, across a biological barrier, and methods of use thereof.

BACKGROUND

The complex design and difficulty in predicting functionality of alpha helical amphipathic peptides for the delivery of anionic cargo has resulted in exploration of more simplistic peptide designs.

The success of arginine-rich peptides such as oligoarginines (e.g. $R_8$— SEQ ID NO:7) indicates that an amphipathic nature is not essential for cell penetration. For example, in the case of Penetratin, it is the cationic nature rather than the helical structure that is responsible for cell penetration [1]. Therefore, increasingly, attention has been paid to developing simple linear peptides rich in cationic amino acids, particularly arginine, that can act as cell penetrating peptides (CPP), or cell delivery agents.

The superiority of arginine over other basic residues, such as lysine and histidine, has led to the conclusion that the guanidine moiety of arginine is crucial for cell entry [2]. Cellular entry is initiated when the positively charged guanidinium groups attach to negatively charged groups (e.g. lipid head groups or proteoglycans such as heparan sulphate) on the cell membrane surface through electrostatic forces, resulting in consequent formation of bidentate hydrogen bonding [3]. Following the initial electrostatic interaction, the CPP-cargo molecule is thought to enter the lipid bilayer as a CPP-cargo-phospholipid complex with the positively charged guanidinium group bound to the phosphate groups of the phosphatidylcholine (PC) and/or sphingomyelin (SM) of the outer leaflet of the cell membrane. A 'capacitor' is then formed between the cationic arginine residues and the anionic phosphatidylserine creating an electric field strong enough to form a reversible pore, which allows the CPP-cargo to pass through the membrane. It is proposed that, as the peptide-cargo complex moves through the membrane, the gradient of the electric field changes which closes this reversible pore within milliseconds [4].

Arginine-rich peptides are excellent for DNA binding and cell penetration. However, if entering cells via an endosomal route, ability to escape the endosome will be a major limiting step of transfection and must be considered because the harsh endosomal environment may lead to degradation of the peptide and cargo. Arginine-rich peptides, such as TAT (SEQ ID NO:8) and R9 (SED ID NO:9), have been shown to lack the ability to escape the endosome unaided, rendering poor transfection efficiencies [5].

Histidine-rich peptides are usually endosomolytic in nature and can facilitate endosomal escape through either the proton sponge or 'flip-flop' effects, according to the number of histidine residues or the arrangement of the residues in a peptide [6]. In a study conducted by Wang et al, the addition of histidine residues to TAT (SEQ ID NO:11) increased transgene expression up to 7000-fold in the human glioma cell line U251 [7]. The addition of bafilomycin A1, a known inhibitor of the proton sponge effect for endosomal escape, then reduced the transfection efficiency significantly, supporting the idea that the activity of histidine as an endosomal escape motif could improve the transfection efficiency of TAT (SEQ ID NO:8). In a study by Mann et al, histidine-modified arginine peptides exhibited more than 2- to 3-fold higher transfection efficiency than histidine-lysine variants [8]. This study highlighted the importance of histidine for endosomal escape and reinforced the superiority of arginine for transfection over other cationic amino acids such as lysine.

The strong electrostatic forces which bind DNA and a cationic peptide may hinder the release of the cargo upon arrival at the desired site of action. To circumvent this, cysteine residues are included for a more controlled intracellular release of cargo through reduction of disulphide bonds in the intracellular environment [9]. It has been reported that the intracellular concentration of glutathione (GSH) influences the reduction of disulphide bonds formed by cysteine residues [10]. Sharma et al observed a reduction in transfection efficiency with cysteine containing peptides Mgpe-9 and Mgpe-delivering pDNA (plasmid DNA) when cells were treated with BSO (Buthionine sulfoximine), a glutamyl-S-transferase inhibitor, indicating the polyplexes were stabilised by disulphide bonds and intra-cellular GSH triggered release of the genetic cargo for successful transfection [11]. Similarly, BSO inhibited cleavage of the disulphide cross linkages in STR-$CH_2R4H_2C$/pLuc complexes resulting in significantly reduced transfection [12]. The addition of cysteine residues has been credited for improved transfection efficiency. Lo et al produced the peptide CHSTATHSC (SEQ ID NO:10) that showed up to 1000-fold higher levels of transgene expression when compared to TAT-10H (SED ID NO:11) peptide that contained no cysteine residues. CHSTATHSC (SEQ ID NO:10) also showed no significant difference in transfection efficiency when compared to PEI 25 kDa (transfection reagent), whilst also exhibiting significantly less toxicity [7]. Similar effects where shown by Mann et al, as transfection efficiency was increased by several orders of magnitude when cysteine residues were added to arginine- and histidine-containing peptides [8].

Cysteine residues may also have an effect on the stability of complexes. Enhanced stability of peptide/pDNA may be achieved by incorporation of terminal cysteine residues, enabling covalent but reversible peptide polymerisation through introduction of twin disulphide bonds [13]. This effect was observed with peptide motifs C—X—C where X is any amino acid, but the effect was most pronounced for peptides containing arginine residues i.e. C—R—C [14]. Another concept, introduced by Bode et al, uses cysteine residues to conjugate truncated peptides which may lead to control over the moment of uptake of CPPs [15]. Truncated arginine peptides conjugated by disulphide bridges using cysteine residues showed varied uptake mechanisms depending on the position of the disulphide bridge, the amount of arginine present in the peptide and the hydrophobicity.

An increase in the hydrophobic character of arginine-rich peptides has been shown to improve uptake efficiency. For example, the counter-ion pyrenebutyrate enhanced the ability of oligoarginines to cross lipid bilayers and enter cells by increasing the hydrophobicity of the hydrophilic arginine-rich peptides [16].

In this invention, peptides have been designed in an attempt to create cell penetrating peptides which can bind and package nucleic acids into nanoparticles for delivery into cells, resulting in impressive transfection, while limiting the cost of production.

Statements of the Invention

According to a first general aspect of the invention, there is provided a peptide comprising, or consisting of:

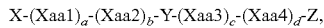

in which each of X and Z is independently selected from Asn, Cys, Gln, Gly, Ser, Thr and Tyr;
in which one of $Xaa_1$ and $Xaa_2$ is His and the other of $Xaa_1$ and $Xaa_2$ is Arg;
in which one of $Xaa_3$ and $Xaa_4$ is His and the other of $Xaa_3$ and $Xaa_4$ is Arg;
in which the amino functional group of X is, optionally, acylated;
in which the carboxylate functional group of Z is, optionally, amidated;
in which Y is selected from Ala and Trp;
in which each of a and d is independently 2 to 4; and each of b and c is independently 2 to 4, or a salt or amide thereof.

Optionally, $Xaa_2$ and $Xaa_3$ are each Arg.
Optionally, Xaa1 and Xaa4 are each His.
By $(His)_a$ is meant, for example, a series of 2 to 4 His amino acid residues without any intervening non-His amino acid residues.
Optionally, each of a and d is identical and is 2 to 4.
Optionally, each of a and d is 3.
Optionally, each of b and c is identical and is 2 to 4.
Optionally, each of b and c is 3.
Optionally, each of a, b, c and d is 3.
Optionally, each of X and Z is identical and selected from Asn, Cys, Gln, Gly, Ser, Thr and Tyr.
Optionally, each of X and Z is Cys.
Optionally, Y is Trp.
Optionally, the sum of b plus c is at least six, so that the peptide comprises a minimum of six arginine (Arg) residues.
Optionally, the sum of a plus d is at least six, so that the peptide comprises a minimum of six histidine (His) residues.
Optionally, the peptide comprises a net positive charge of 6 to 8. Further optionally, the peptide comprises a net positive charge of 6.
Further optionally, the peptide is Cys-$(His)_3$-$(Arg)_3$-Trp-$(Arg)_3$-$(His)_3$-Cys (CHHHRRRWRRRHHHC) (SEQ ID NO: 4).
Optionally, the peptide comprises 8 to 20 amino acids. This limits peptide sequence length, while maintaining cell penetrating function and cationic nature.
Optionally, the peptide comprises
4 to 8 arginine residues (optionally 6 arginine residues);
1 tryptophan or alanine residue (optionally a tryptophan residue) at the core to improve hydrophobic interaction with cell membranes;
1 amino acid, at each end, selected from Asn, Cys, Gln, Gly, Ser, Thr and Tyr to enhance stability and cargo release once inside cell;
0 to 8 Histidine residues at the core (optionally 4 to 8 histidine residues; further optionally 6 histidine residues) for pH dependent 'flip-flop' effect for endosomal escape; and
optionally, one amino acid selected from Asp and Glu adjacent the amino acid, at each end, that is selected from Asn, Cys, Gln, Gly, Ser, Thr and Tyr.

Suitably, the present invention provides a peptide comprising or consisting of:

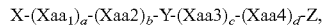

where X and Z are Cys,
Xaa1 and Xaa4 are His; a and d are each independently 2 to 4;
Xaa2 and Xaa3 are Arg; b and c are each independently 2 to 4; and
Y is Trp, or a salt, or amide thereof.
For example, the peptide may comprise or consist of:

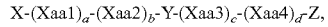

where X and Z are Cys,
Xaa1 and Xaa4 are His; a and d are each independently 2 to 4;
Xaa2 and Xaa3 are Arg; b and c are each independently 3 or 4; and
Y is Trp, or a salt, or amide thereof.
Suitably, the peptide comprises or consists of:

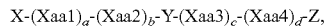

where X and Z are Cys,
Xaa1 and Xaa4 are His; a and d are each independently 3 or 4;
Xaa2 and Xaa3 are Arg; b and c are each independently 3 or 4; and
Y is Trp, or a salt, or amide thereof.
In some aspects the peptide of the present invention may comprise an amide derived from a fatty acid, for example, a stearoyl group may be tethered to the peptide of the invention. Suitably, when Y is Trp, the indole ring may be N-alkylated. For example, the tryptophan indole ring may comprise a C1-C6 alkyl group tethered to the nitrogen of the indole ring.

According to a second aspect of the invention, there is provided a peptide of the first aspect of the invention, for use as a cell delivery agent i.e. for delivering agents, such as therapeutics into cells. Suitably, the therapeutic may be a nucleic acid, for example, DNA, RNAi, mRNA, miRNA, saRNA.

According to a third aspect of the invention, there is provided the use of the peptide of the first aspect of the invention for the delivery of an anionic cargo to a cell or subject in need thereof.

According to a fourth aspect of the invention, there is provided a peptide of the first aspect of the invention for use in inducing an immune response in a subject in need thereof or a method for inducing an immune response in a subject comprising the administration of the peptide of the first aspect of the invention to a subject in need thereof.

According to a fifth aspect of the invention, there is provided a peptide of the first aspect of the invention for use in gene therapy in a subject in need thereof.

According to a sixth aspect of the invention, there is provided a peptide of the first aspect of the invention for use in the treatment and/or prophylaxis of an infection, cancer, wounds in a subject in need thereof or a method for the treatment and/or prophylaxis of an infection, cancer, wounds comprising the administration of the peptide of the first aspect of the invention to a subject in need thereof. Suitably, the cancer is selected from: breast cancer, prostate cancer, brain cancer, lung cancer, pancreatic cancer, ovarian cancer or skin cancer. For example, the cancer may be breast cancer or prostate cancer.

DETAILED DESCRIPTION

Peptide design was carried out in an attempt to create a cell penetrating peptide which can bind and package anionic cargo, such as nucleic acids, into nanoparticles suitable for gene delivery. Peptides were designed in pairs to allow direct comparison and analysis of functionality based on specific amino acid sequence differences. The sequences of the novel linear peptides are shown in Table 1.

TABLE 1

Sequences of novel linear peptides

| Peptide name | Sequence |
|---|---|
| Peptide 7 | CRRRWHHHHHWRRRC (SEQ ID NO: 1) |
| Peptide 8 | CWRRRHHHHHRRRWC (SEQ ID NO: 2) |
| Peptide 9 | CHRHRHRWHRHRHRC (SEQ ID NO: 3) |

TABLE 1-continued

Sequences of novel linear peptides

| Peptide name | Sequence |
|---|---|
| Peptide 10 | CHHHRRRWRRRHHHC (SEQ ID NO: 4) |
| Peptide 11 | CRRRRWRRRRC (SEQ ID NO: 5) |
| Peptide 12 | CEHHRRRWRRRHHEC (SEQ ID NO: 6) |

These six linear peptides have been designed to have similar sequences with slight differences and grouped into pairs to allow direct comparisons. See Table 2 for a summary of peptide similarities and differences. Peptides 7 to 9, 11 and 12 are outside the scope of the present invention.

TABLE 2

Summary of novel peptide pairing to allow comparison of sequences and design rationale.

| Peptide pair | Sequence comparison | Rationale |
|---|---|---|
| 7 and 8 (15-mer) | 7: CRRRWHHHHHWRRRC (SEQ ID NO: 1) 8: CWRRRHHHHHRRRWC (SEQ ID NO: 2) | Histidine residues at the core of the peptide sequence flanked by arginine. Two tryptophan residues included for enhanced interaction with cell membranes. Tryptophan residues at different positions to assess optimal sequence and positioning. |
| 9 and 10 (15-mer) | 9: CHRHRHRWHRHRHRC (SEQ ID NO: 3) 10: CHHHRRRWRRRHHHC (SEQ ID NO: 4) | Arginine and histidine residues arranged in either alternating or block sequence to assess impact on functionality. Arginine block positioned at the core of the sequence, flanked by histidine at each end-in contrast to positioning in Peptide 7 and 8. Tryptophan positioned in the middle to assess positioning-in contract to positioning in Peptide7 and 8 FIG. 5c shows that Peptide 9 has poor transfection, compared to FIG. 5d which shows the same amino acids, but in a block sequence, having higher transfection. |
| 11 (11-mer) and 12 (15-mer) | 11: CRRRRWRRRRC (SEQ ID NO: 5) 12: CEHHRRRWRRRHHEC (SEQ ID NO: 6) | Assessment of endosomal escape functionality of histidine Histidine removed from Peptide 11 to assess if endosomal escape is possible without Histidine residues Peptide 12 designed to include two glutamic acid residues reported to be involved in endosomal escape mechanisms in amphipathic peptides |

The ProtParam tool was used to compute the possible physical and chemical properties of each peptide and the results for Peptides 7 and 8 are shown in Table 3, Peptides 9 and 10 in Table 4 and Peptide 11 and 12 in Table 5. Parameters such as molecular weight and number of positively charged residues were then used when calculating N:P ratios for each peptide.

TABLE 3

Computed properties of Peptide 7 and 8

| Properties | Peptide 7 | Peptide 8 |
|---|---|---|
| Number of amino acids | 15 | 15 |
| Molecular weight (Daltons) | 2219.5 Da | 2219.5 Da |
| Theoretical isoelectric point (pI) | 12.0 | 12.0 |
| Amino acid composition | Arg (R) – 6 = 40% Cys (C) – 2 = 13.3% His (H) – 5 = 33.3% Trp (W) – 2 = 13.3% | Arg (R) – 6 = 40% Cys (C) – 2 = 13.3% His (H) – 5 = 33.3% Trp (W) – 2 = 13.3% |

TABLE 3-continued

Computed properties of Peptide 7 and 8

| Properties | Peptide 7 | Peptide 8 |
| --- | --- | --- |
| Total number of negatively charged residues (Asp + Glu): | 0 | 0 |
| Total number of positively charged residues (Arg + Lys): | 6 | 6 |
| Instability index | 214.13 (unstable) | 228.89 (unstable) |
| Grand average of hydropathicity | −2.653 (hydrophilic) | −2.653 (hydrophilic) |

TABLE 4

Computed properties of Peptide 9 and 10

| Properties | Peptide 9 | Peptide 10 |
| --- | --- | --- |
| Number of amino acids | 15 | 15 |
| Molecular weight (Daltons) | 2170.48 Da | 2170.48 Da |
| Theoretical Isoelectric point (pI) | 12.0 | 12.0 |
| Amino acid composition | Arg (R) − 6 = 40%<br>Cys (C) − 2 = 13.3%<br>His (H) − 6 = 40.%<br>Trp (W) − 1 = 6.7% | Arg (R) − 6 = 40%<br>Cys (C) − 2 = 13.3%<br>His (H) − 6 = 40.%<br>Trp (W) − 1 = 6.7% |
| Total number of negatively charged residues (Asp + Glu): | 0 | 0 |
| Total number of positively charged residues (Arg + Lys): | 6 | 6 |
| Instability index | 136.40 (unstable) | 234.84 (unstable) |
| Grand average of hydropathicity | −2.807 (hydrophilic) | −2.807 (hydrophilic) |

TABLE 5

Computed properties of Peptide 11 and 12

| Properties | Peptide 11 | Peptide 12 |
| --- | --- | --- |
| Number of amino acids | 11 | 15 |
| Molecular weight (Daltons) | 1660.01 Da | 2154.43 Da |
| Theoretical Isoelectric point (pI) | 12.22 | 11.31 |
| Amino acid composition | Arg (R) − 8 = 40%<br>Cys (C) − 2 = 18.2%<br>Trp (W) − 1 = 9.1% | Arg (R) − 6 = 40%<br>Cys (C) − 2 = 13.3%<br>Glu (E) − 2 = 13.3%<br>His (H) − 4 = 26.7%<br>Trp (W) − 1 = 6.7% |
| Total number of negatively charged residues (Asp + Glu): | 0 | 2 |
| Total number of positively charged residues (Arg + Lys): | 8 | 6 |
| Instability index | 373.60 (unstable) | 237.37 (unstable) |
| Grand average of hydropathicity | −2.900 (hydrophilic) | −2.847 (hydrophilic) |

Peptides 7 to 9, 11 and 12 are outside the scope of the present invention.

Anionic Cargo

In a general context, the anionic cargo may be selected from a nucleic acid or small molecule agent such as a phosphonate drug or phosphate drug, such as a bisphosphonate, a diphosphate, triphosphate drug.

For example, the anionic cargo may be an organophosphate, optionally with a molecular weight between 0.15 and 2.5 kDa.

According to one embodiment, the anionic cargo may be an alkali metal, or alkaline earth metal, bisphosphate, diphosphate, or triphosphate, preferably an alkaline earth metal bisphosphate, diphosphate, or triphosphate.

In one aspect, the bisphosphonate may be etidronate, clodronate, tiludronate, pamidronate, neridronate, olpadronate, alendronate, ibandronate, risedronate, zoledronate, or any derivative of these compounds.

In another aspect, the diphosphate may be based on a nucleotide or a nucleoside such as didanosine, vidarabine, emtricitabine, lamivudine, zalcitabine, abacavir, acyclovir, entecavir, stavudine, telbivudine, zidovudine, idoxuridine, trifluridine, ganciclovir, valganciclovir, ciclovir, aciclovir, azacitidine, decitabine, zebularine, cytarabine, gemcitabine, troxacitibine, CNDAC (2'-C-cyano-2'-deoxy-1-p-D-arabino-pentofuranosylcytosine), fludarabine, cladribine, clofarabine, pentostatin, forodesine, azidothymidine, edoxudine, and/or any derivative of these compounds.

For example, the diphosphate may be selected from one or more of the following isopentenyl pyrophosphate (IPP), (E)-4-Hydroxy-3-methyl-but-2-enyl pyrophosphate (HMBPP), (E)-5-hydroxy-4-methylpent-3-enyl pyrophosphate (HDMAPP), Dimethylallyl pyrophosphate (DMAPP), ethyl pyrophosphate (EPP), and associated metabolites such as IPP's triphosphoric acid 1-adenosin-5'-yl ester 3-(3-methylbut-3-enyl) ester (Apppl).

In another aspect the triphosphate may be based on a nucleotide or nucleoside such as didanosine, vidarabine, emtricitabine, lamivudine, zalcitabine, abacavir, acyclovir, entecavir, stavudine, telbivudine, zidovudine, idoxuridine, trifluridine, ganciclovir, valganciclovir, ciclovir, aciclovir, azacitidine, decitabine, zebularine, cytarabine, gemcitabine, troxacitibine, CNDAC (2'-C-cyano-2'-deoxy-1-p-D-arabino-pentofuranosylcytosine), fludarabine, cladribine, clofarabine, pentostatin, forodesine, azidothymidine, edoxudine, or any derivative of these compounds.

For example, the triphosphate may be based on a diphosphate or pyrophosphate such as isopentenyl pyrophosphate (IPP), (E)-4-Hydroxy-3-methyl-but-2-enyl pyrophosphate (HMBPP), (E)-5-hydroxy-4-methylpent-3-enyl pyrophosphate (HDMAPP), Dimethylallyl pyrophosphate (DMAPP), ethyl pyrophosphate (EPP), and associated metabolites such as IPP's triphosphoric acid 1-adenosin-5'-yl ester 3-(3-methylbut-3-enyl) ester (Apppl).

In another aspect, the anionic cargo is a nucleic acid selected from DNA, pDNA, RNA, mRNA, siRNA, shRNA, saRNA, miRNA, a plasmid vector, or a nucleic acid aptamer.

Uses

It will be understood that the peptide of the first aspect of the invention may be used as a cell delivery agent.

Additionally, the peptide of the first aspect of the invention may be for use in inducing an immune response in a subject in need thereof.

Still additionally, the peptide of the first aspect of the invention may be for use in gene therapy in a subject in need thereof.

Still further additionally, the peptide of the first aspect of the invention may be for use in the treatment and/or prophylaxis of an infection, cancer, wounds in a subject in need thereof.

Finally, the peptide of the first aspect of the invention could be used to deliver therapies for the treatment and/or prophylaxis of an infection, cancer, wounds from polymeric medical devices.

FIGURE LEGENDS

Figure 1:
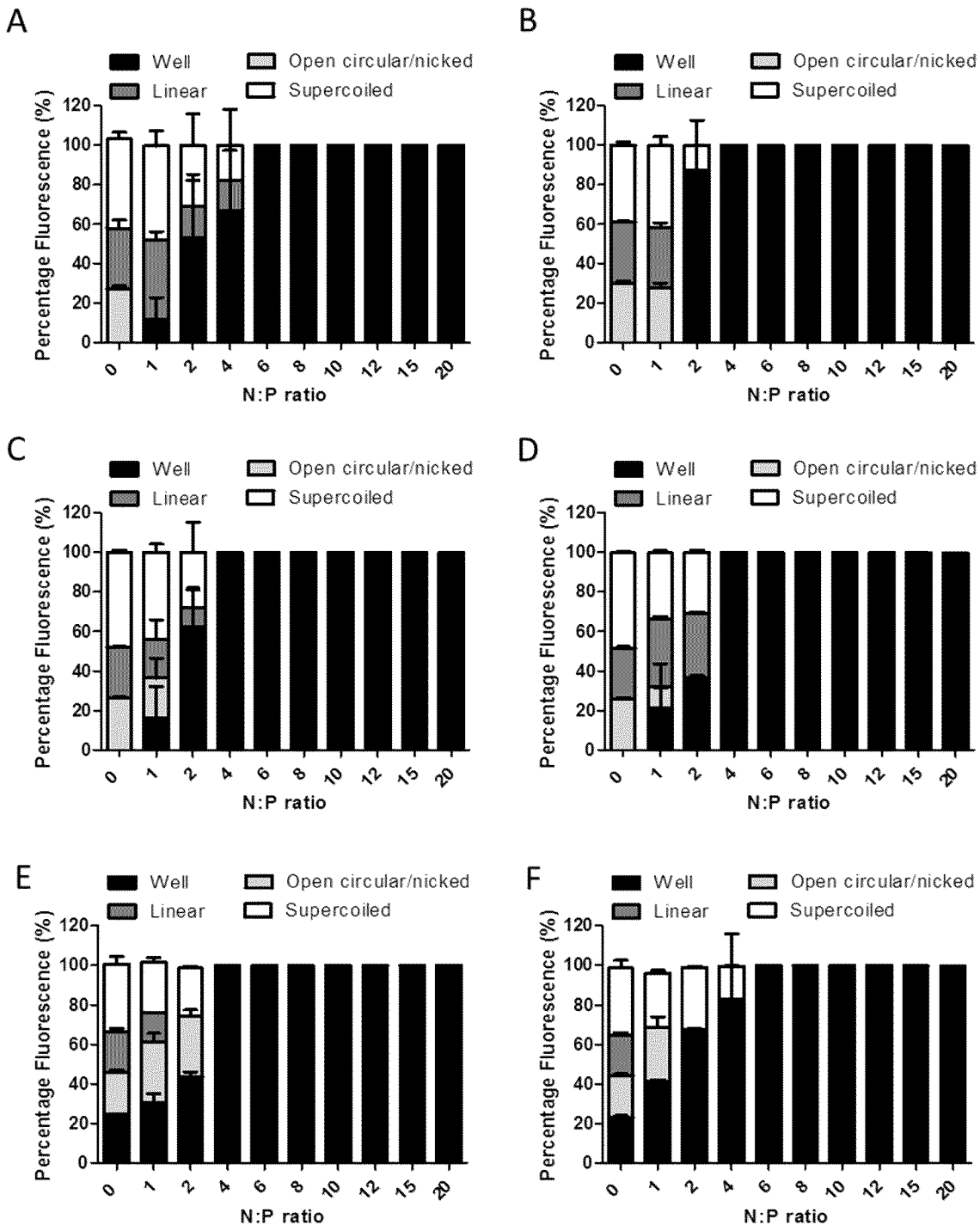

FIG. 1: Densitometry of gel electrophoresis assay using 1% Agarose Gel stained with ethidium bromide for fluorescence for A) Peptide 7, B) Peptide 8, C) Peptide 9, D) Peptide 10, E) Peptide 11 and F) Peptide 12 analysed using Image J software. Densitometry was used to determine relative fluorescence detected in the agarose gel with respect to characteristic pDNA conformation bands (i.e. supercoiled (unshaded), open circular/nicked (lightly shaded) or linear conformation (darkly shaded)). Image J software was used to analyse fluorescence and calculated as a percentage of the naked pDNA control (N:P 0). Results are displayed as mean±SEM, n=3.

Figure 2:
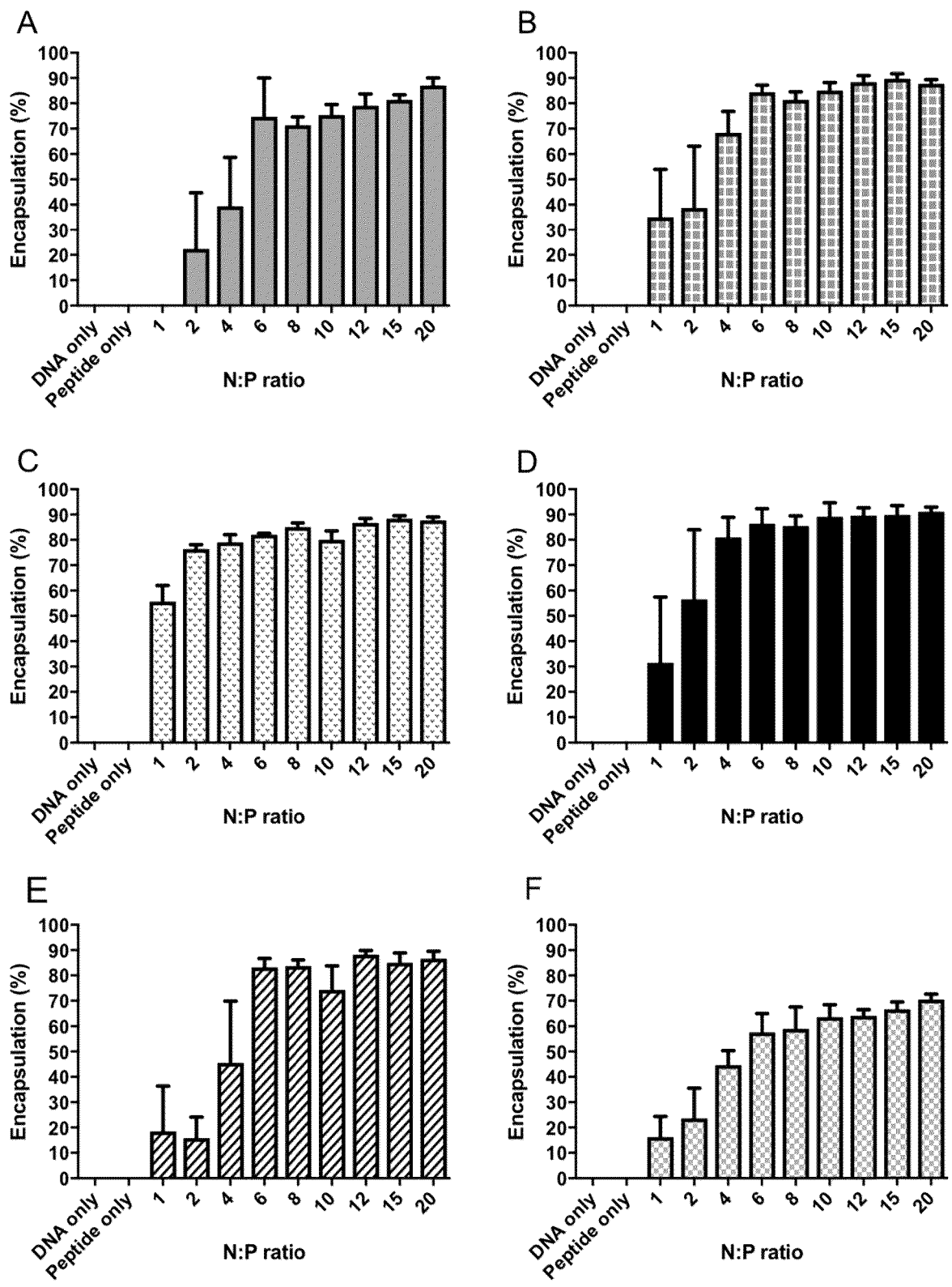

FIG. 2: DNA complexation efficiency assay using Quant-iT™ PicoGreen® reagent indicating the efficiency of A) Peptide 7, B) Peptide 8, C) Peptide 9, D) Peptide 10, E) Peptide 11 and F) Peptide 12 to complex 0.5 µg pEGFP-N1 (Accession Number: U55762.1) (a pDNA) at a range of N:P ratios. Peptide/pEGFP-N1 complexes were prepared at a range of N:P ratios from 1 to 20. 50 µl samples of each N:P ratio was pipetted into a 96-well plate with Quant-iT™ PicoGreen® reagent. Sample fluorescence was then analysed by excitation at 480 nm and the fluorescence emission intensity measured at 520 nm using a Synergy 2 Multi-Mode Microplate Reader. Fluorescence was then calculated as a percentage of the control and converted to the percentage DNA complexed. Results are displayed as mean±SEM, n=3.

Figure 3:
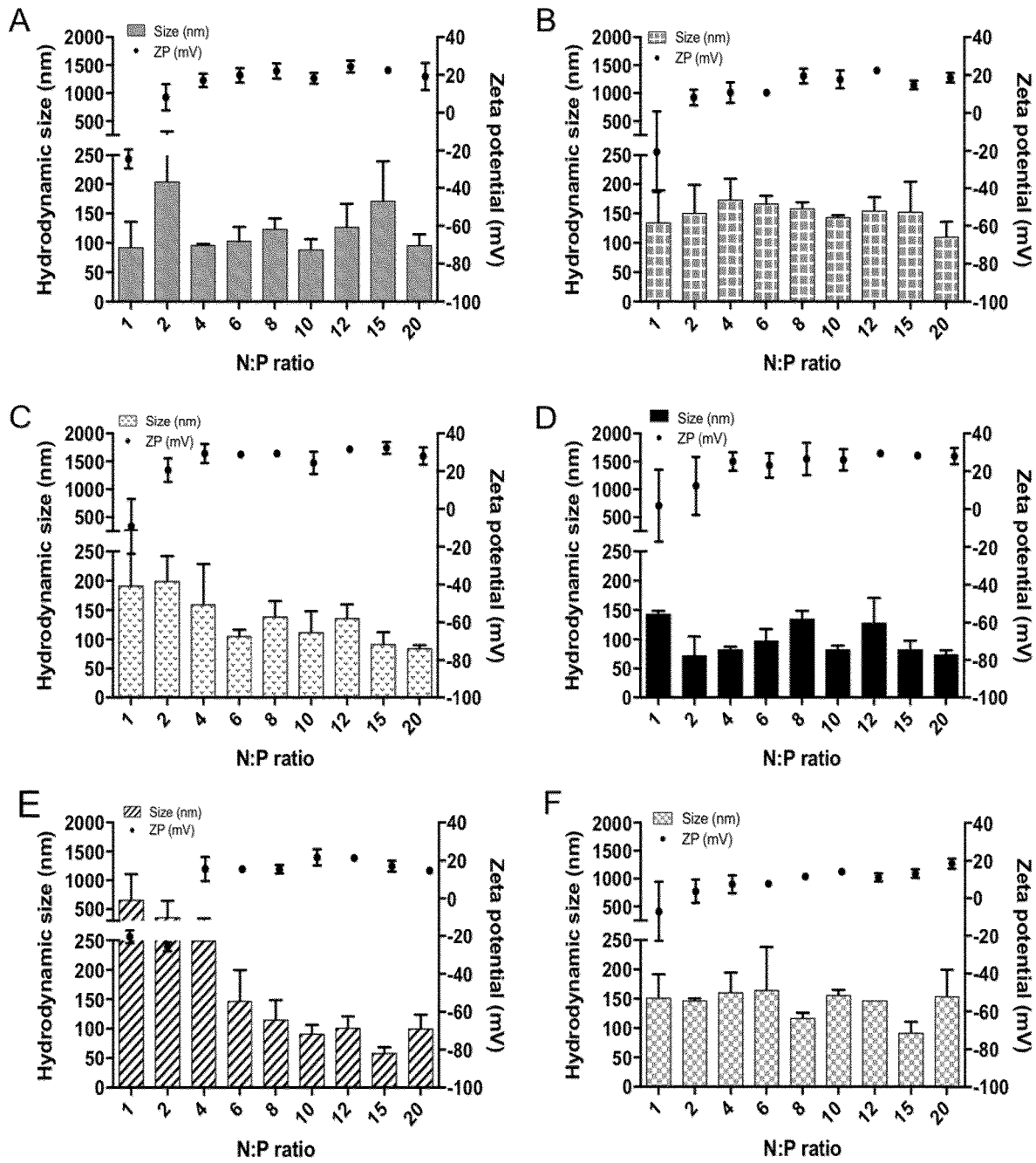

FIG. 3: Mean hydrodynamic size and zeta potential of nanoparticles prepared with pEGFP-N1 and A) Peptide 7, B) Peptide 8, C) Peptide 9, D) Peptide 10, E) Peptide 11 or F) Peptide 12 at a range of N:P ratios. For example, at an N:P ratio of 10 with Peptide 7, nanoparticles comprise 0.5 µg of pEGFP-N1 and 5.7 µg Peptide 7. Nanoparticles were made up to 50 µl with molecular grade water and incubated for 30 min at room temperature before hydrodynamic size and zeta potential were measured using a Malvern Zetasizer Nano ZS instrument. Results are displayed as mean±SEM, n=3.

Figure 4:
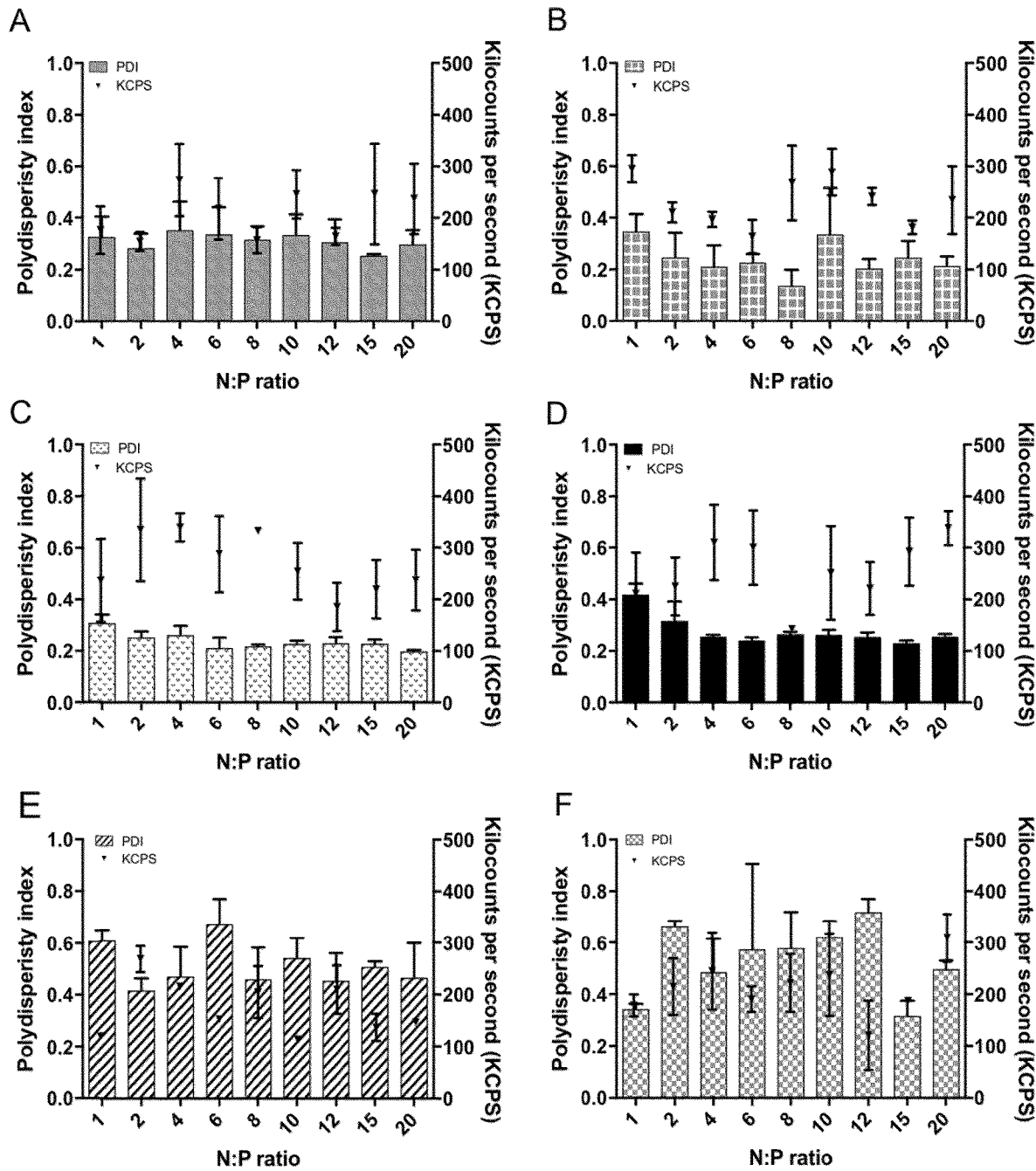

FIG. 4: Polydispersity index (PDI) and particle count (kilocounts per second) of nanoparticles prepared with pEGFP-N1 and A) Peptide 7, B) Peptide 8, C) Peptide 8, D) Peptide 10, E) Peptide 11 or F) Peptide 12 at a range of N:P ratios corresponding to size and zeta potential analysis in FIG. 3. Nanoparticles were made up to 50 µl with molecular grade water and incubated for 30 min at room temperature before PDI and particle count were measured using a Malvern Zetasizer Nano ZS instrument. Results are displayed as mean±SEM, n=3.

Figure 5:
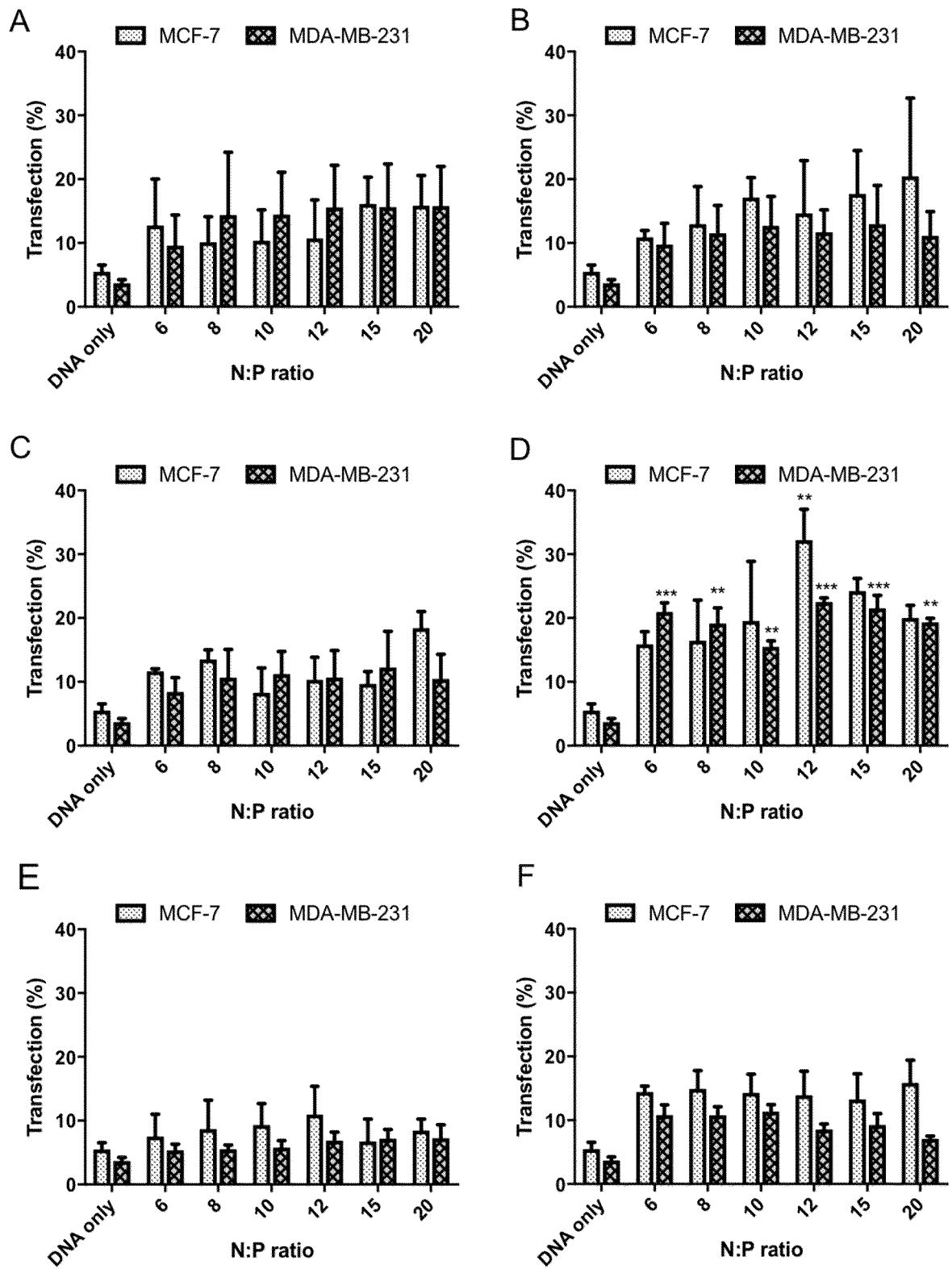

FIG. 5: Transfection efficiency of nanoparticles comprising pEGFP-N1 and A) Peptide 7, B) Peptide 8, C) Peptide 9, D) Peptide 10, E) Peptide 11 and F) Peptide 12 assessed in MCF-7 and MDA-MB-231 breast cancer cells. Cells were transfected for 4 h with peptide/pEGFP-N1 nanoparticles at a range of N:P ratios. Following transfection, medium was replaced with DMEM supplemented with 10% FCS and incubated for 48 h before quantification of transfection efficiency by flow cytometry at 4% gating. Results are displayed as mean±SEM, n=3 and statistical analysis was carried out by One-Way ANOVA and Dunnett post-test comparing transfection efficiency of each peptide to DNA only (*=P<0.05,  =P<0.01, *=P<0.001).

Figure 6:
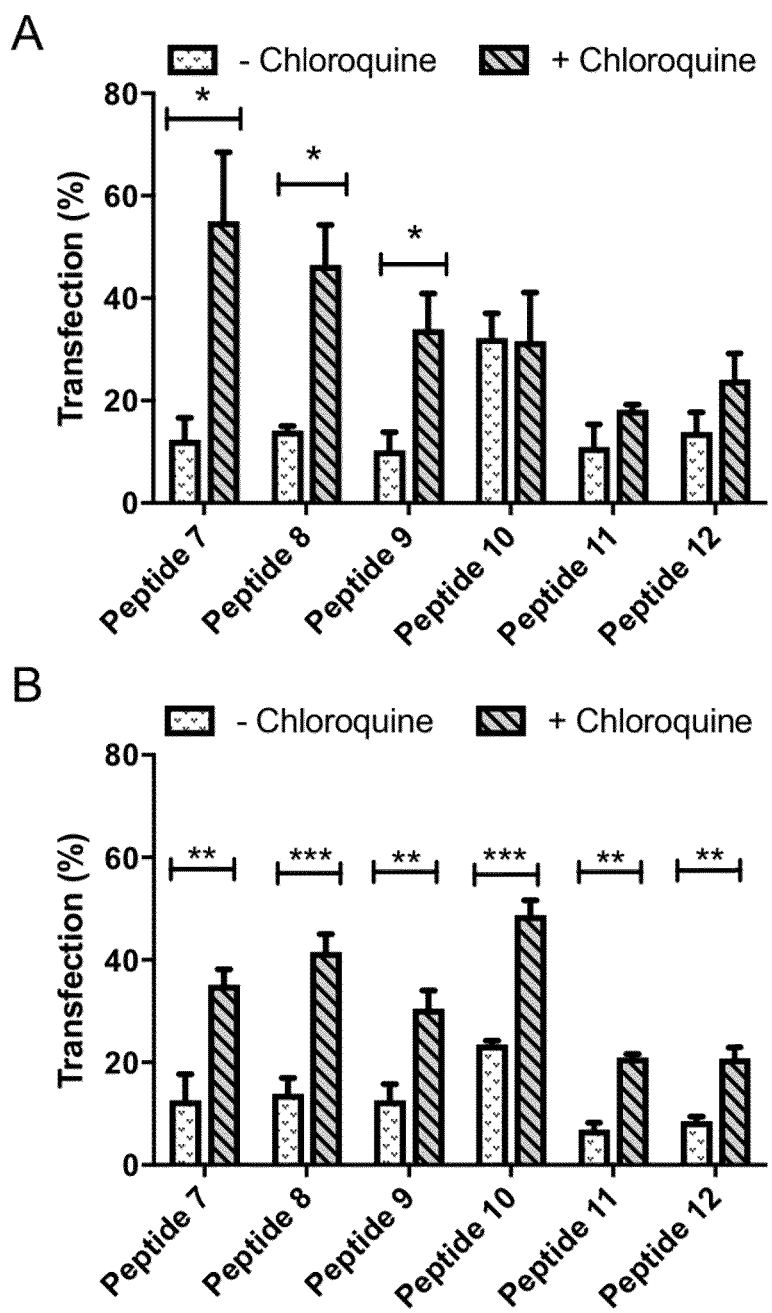

FIG. 6: Transfection efficiency of nanoparticles comprising pEGFP-N1 and Peptides 7 to 12 assessed in A) MCF-7 and B) MDA-MB-231 breast cancer cells with and without chloroquine, a reagent known to facilitate endosomal escape. Cells were transfected for 4 h with peptide/pEGFP-N1 nanoparticles at N:P 10. 10 µM chloroquine was added to cells in appropriate wells along with the nanoparticles. Following transfection, medium was replaced with DMEM supplemented with 10% FCS and incubated for 48 h before quantification of transfection efficiency by flow cytometry at 4% gating. Results are displayed as mean±SEM, n=3. Statistical analysis was carried out using an unpaired t test (*=P<0.05,  =P<0.01, *=P<0.001)

Figure 7:
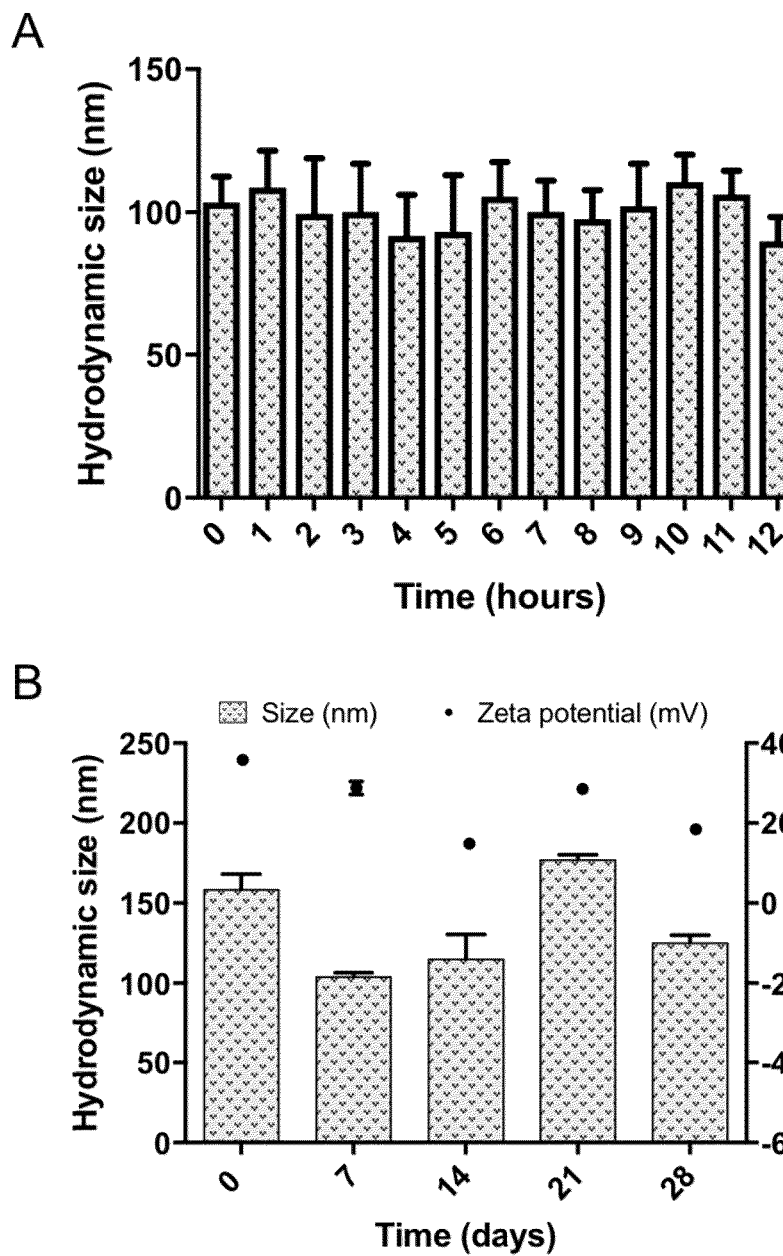

FIG. 7: Mean hydrodynamic size of Peptide 10/pEGFP-N1 nanoparticles was determined to assess stability across A) a 12 h time period and B) a 28-day time period. Nanoparticles were prepared at N:P 12. In the 12 h study, the mean hydrodynamic size was measured at 1 h intervals starting immediately after formulation using a Malvern Zetasizer Nano ZS. For the 28-day study, nanoparticles were prepared on Day 0 and the mean hydrodynamic size and zeta potential were measured every 7 days for 28 days. Results are displayed as mean±SEM, n=3.

Figure 8:
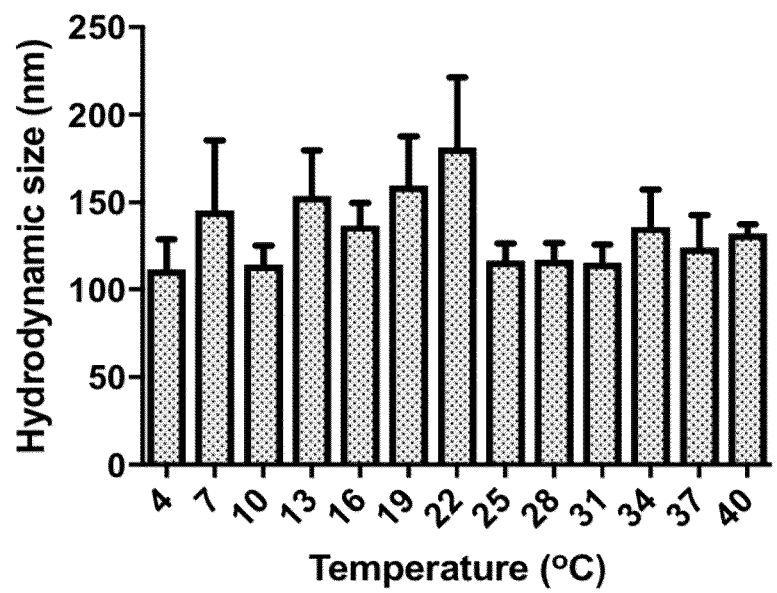
Figure 8:
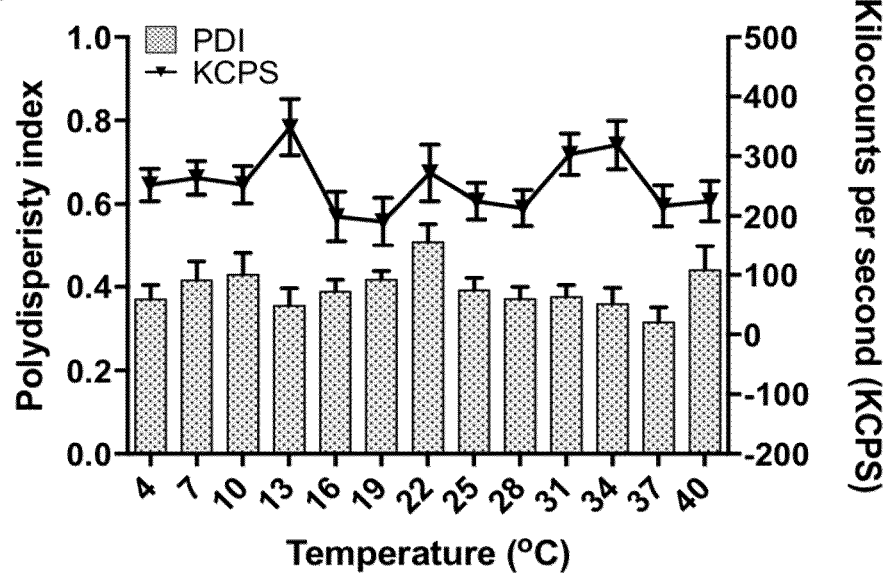

FIG. 8: Mean hydrodynamic size of Peptide 10/pEGFP-N1 nanoparticles over a range of temperatures. Nanoparticles were prepared at N:P 12 and incubated for 30 min before measuring A) hydrodynamic size and B) PDI and particle count using a temperature trend function on the Malvern Zetasizer Nano ZS. Results are displayed as mean±SEM, n=3.

Figure 9:
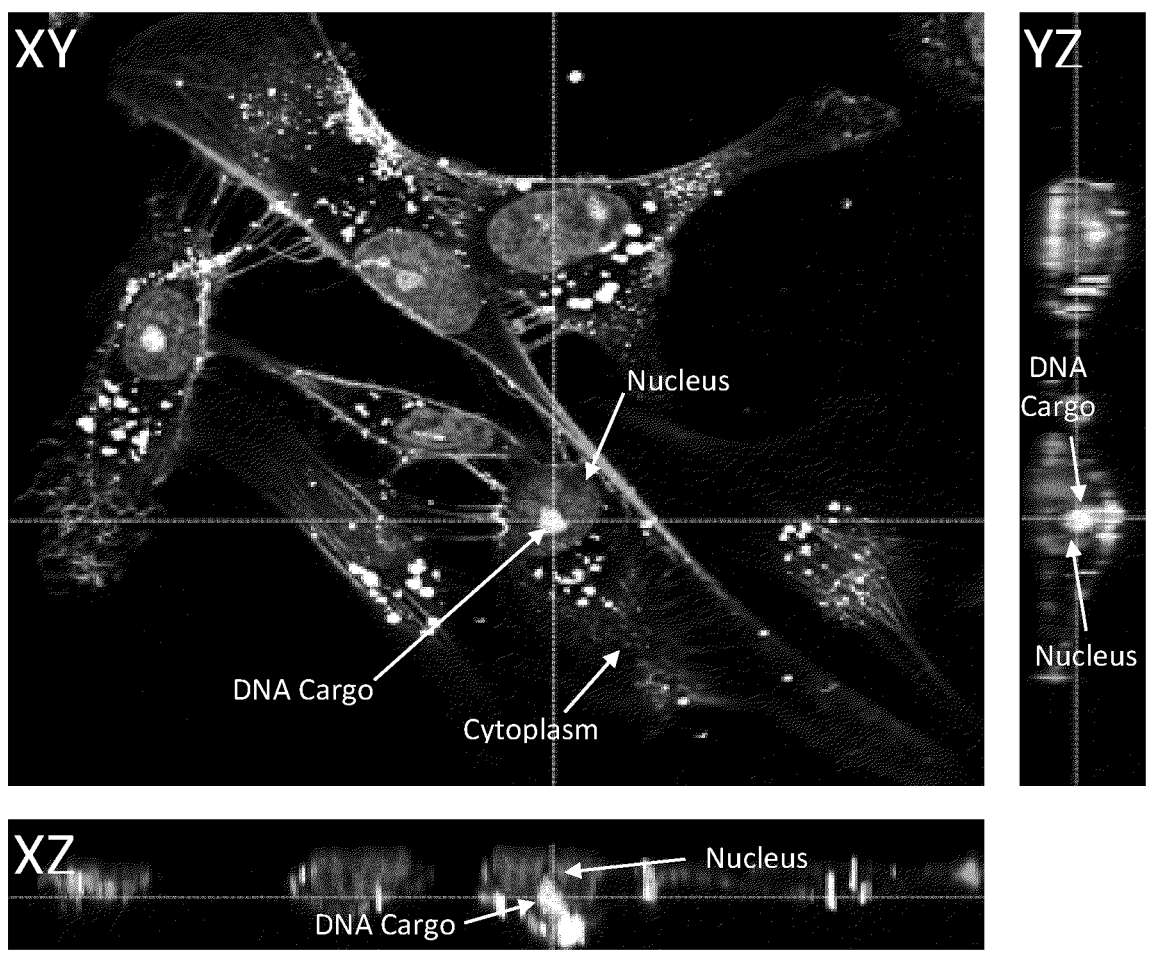

FIG. 9: Confocal microscopy images following transfection of MDA-MB-231 breast cancer cells with Peptide 10 at N:P 12 delivering Cy3 labelled pDNA at 4 h post-transfection. Cells were stained with Fluorescein (FITC)-phalloidin (Life technologies, UK) and treated with ProLong Gold Antifade Mountant with DAPI (Life technologies, UK). Cells were imaged using a TSC SP5-Leica Microsystems confocal microscope (Leica, UK) and analysed using LAS AF Lite Software (Leica, UK). Orthogonal sectioning was used to visualise intra-nuclear presence of Cy3-pDNA. The image is representative of three independent repeats. Nanoparticles are depicted in white.

Figure 10:
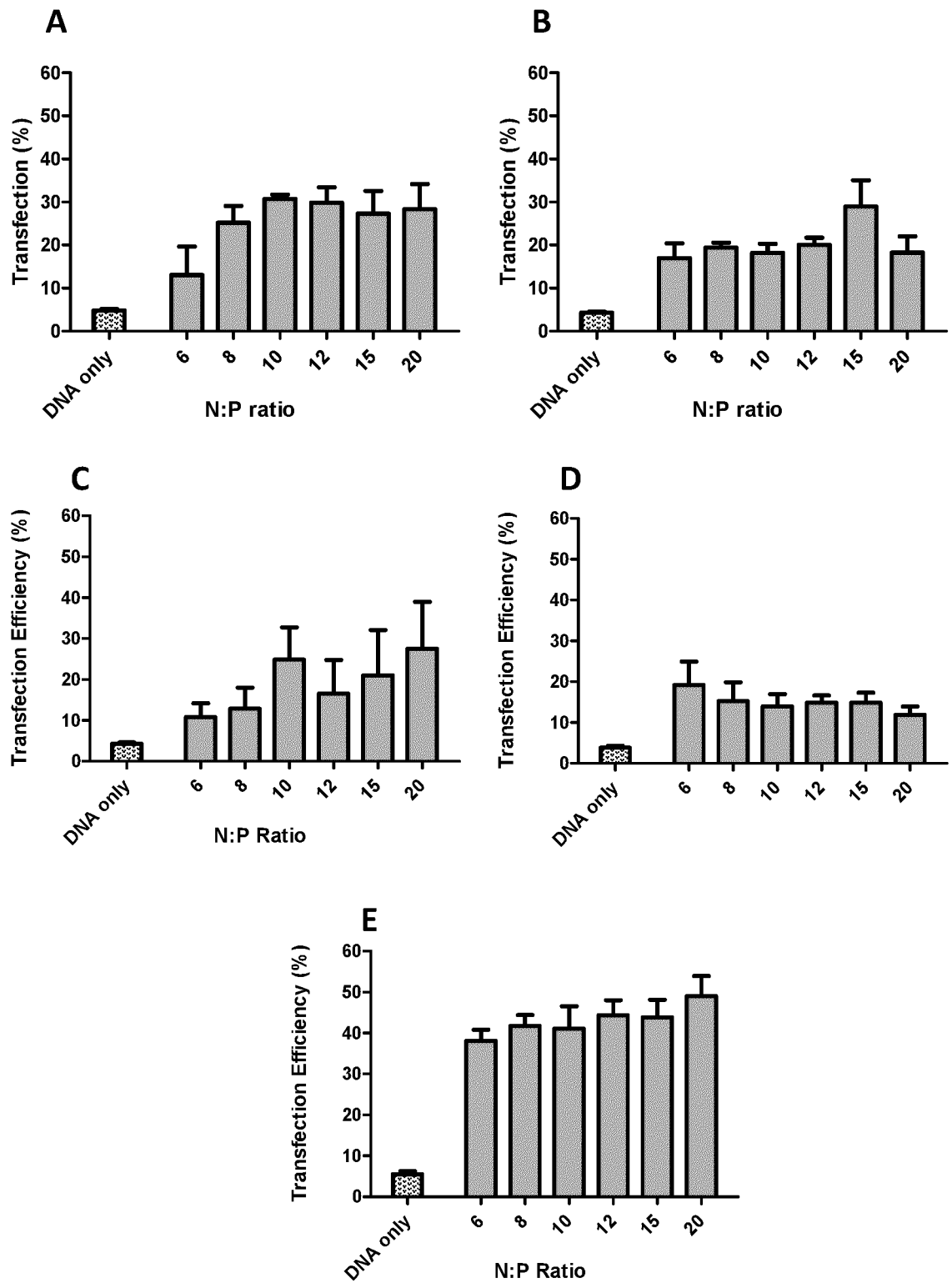

FIG. 10: Transfection efficiency of nanoparticles comprising pEGFP-N1 and Peptide 10 assessed in A) DU145 and B) PC-3 prostate cancer cells, C) NCTC-929 fibroblast, D) HMEC-1 endothelial, and E) HaCaT keratinocyte cells to determine transfection in additional cell lines. Cells were transfected for 4 h with Peptide 10/pEGFP-N1 nanoparticles at a range of N:P ratios. Following transfection, medium was replaced with culture medium supplemented with 10% serum and incubated for 48 h before imaging using i) light and ii) fluorescence microscopy. Scale bar=400 µm. iii) Quantification of transfection efficiency was subsequently analysed by flow cytometry at 4% gating. Results are displayed as mean±SEM, n=3.

Figure 11:
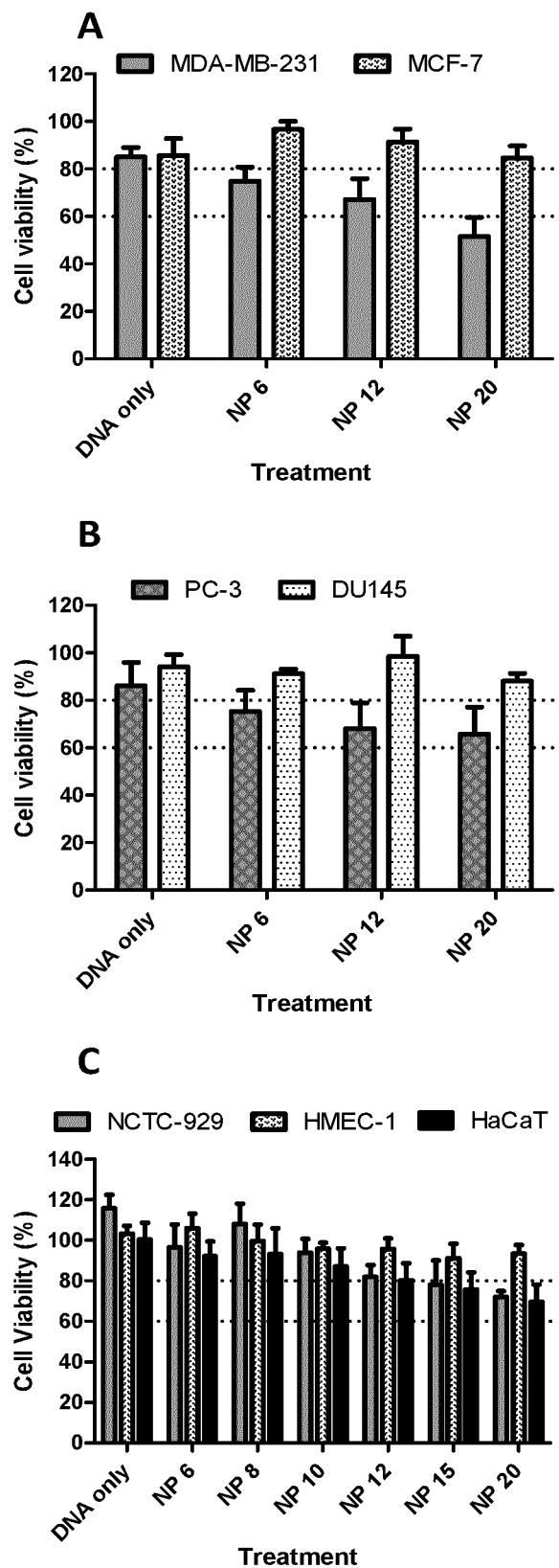

FIG. 11: Cell viability of A) MCF-7 and MDA-MB-231 breast cancer cells, B) DU145 and PC-3 prostate cancer cells, and C) NCTC-929 fibroblast, HMEC-1 endothelial, and HaCaT keratinocyte cells following transfection with Peptide 10. Cells were transfected with Peptide 10 at a range of N:P ratios for 4 h before replacement with complete medium. After 24 h, cells were treated with MTS reagent for 2 h in dark conditions. A Bio-Tek Powerwave XS plate reader was then used to read absorbance at 490 nm with Gen5 software and any background absorbance was subtracted from readings. Untreated cells were considered to be 100% viable and viability under all conditions was calculated relative to this. Results are displayed as mean±SEM, n=3.

Figure 12:
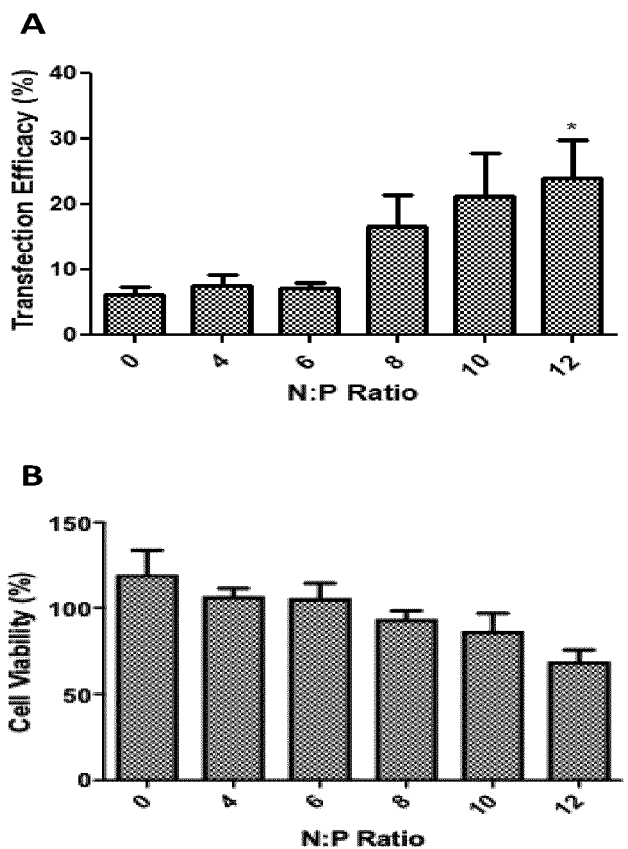

FIG. 12: Transfection efficiency and cell viability of nanoparticles comprising pEGFP-N1 and Peptide 10 assessed in ARPE human retinal cells. (A) Cells were transfected for 4 h with Peptide 10/pEGFP-N1 nanoparticles at a range of N:P ratios. Following transfection, medium was replaced with culture medium supplemented with 10% serum and incubated for 48 h before imaging using i) light and ii) fluorescence microscopy. Scale bar=400 µm. iii) Quantification of transfection efficiency was subsequently analysed by flow cytometry at 4% gating. (B) After 24 h, cells were treated with MTS reagent for 2 h in dark conditions. A Bio-Tek Powerwave XS plate reader was then used to read absorbance at 490 nm with Gen5 software and any background absorbance was subtracted from readings. Untreated cells were considered to be 100% viable and viability under all conditions was calculated relative to this. Results are displayed as mean±SEM, n=3.

Figure 13:
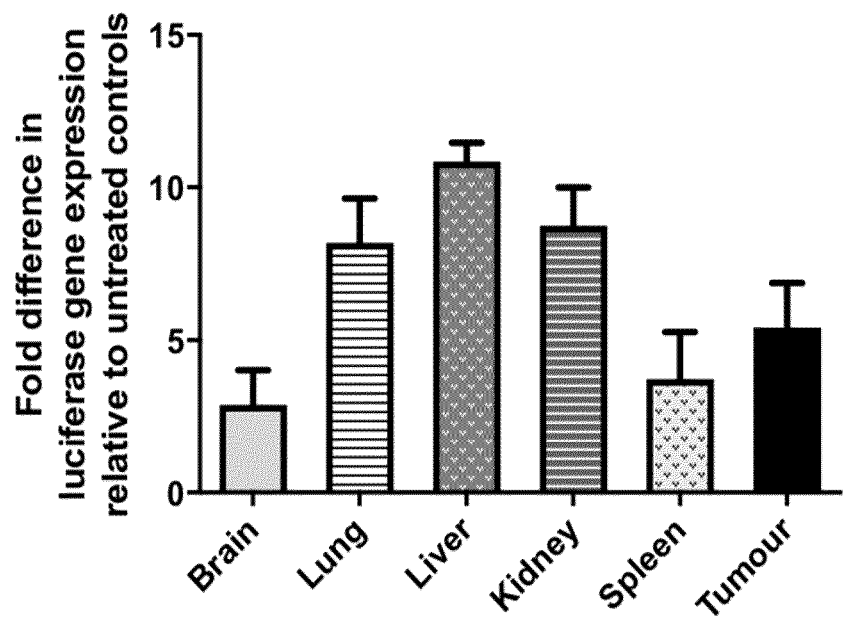

FIG. 13: Ex vivo luciferase tissue distribution 48 h following systemic administration of Peptide 10/pLuc complexes to BALB/c SCID mice bearing MDA-MB-231 xenografts. Peptide 10/pLuc complexes were prepared at N:P 8 (from Table 6, N:P 1 is 1.11; so N:P 8 is 8.88 µg) with 50 µg pLuc (SEQ ID NO:12). Complexes were subsequently administered to BALB/c SCID mice via tail vein injection in a total volume of 200 µl. Mice were sacrificed at 48 h post injection and organs harvested. Quantification of luciferase gene expression in the brain, lungs, liver, kidney, spleen, and tumour was analysed using qRT-PCR. Total mRNA was extracted from organs, reverse transcribed and luciferase expression relative to housekeeper (p-actin) analysed using qRT-PCR. Gene expression is expressed as fold difference relative to untreated control and points represent mean±SEM, n=3.

Figure 14:
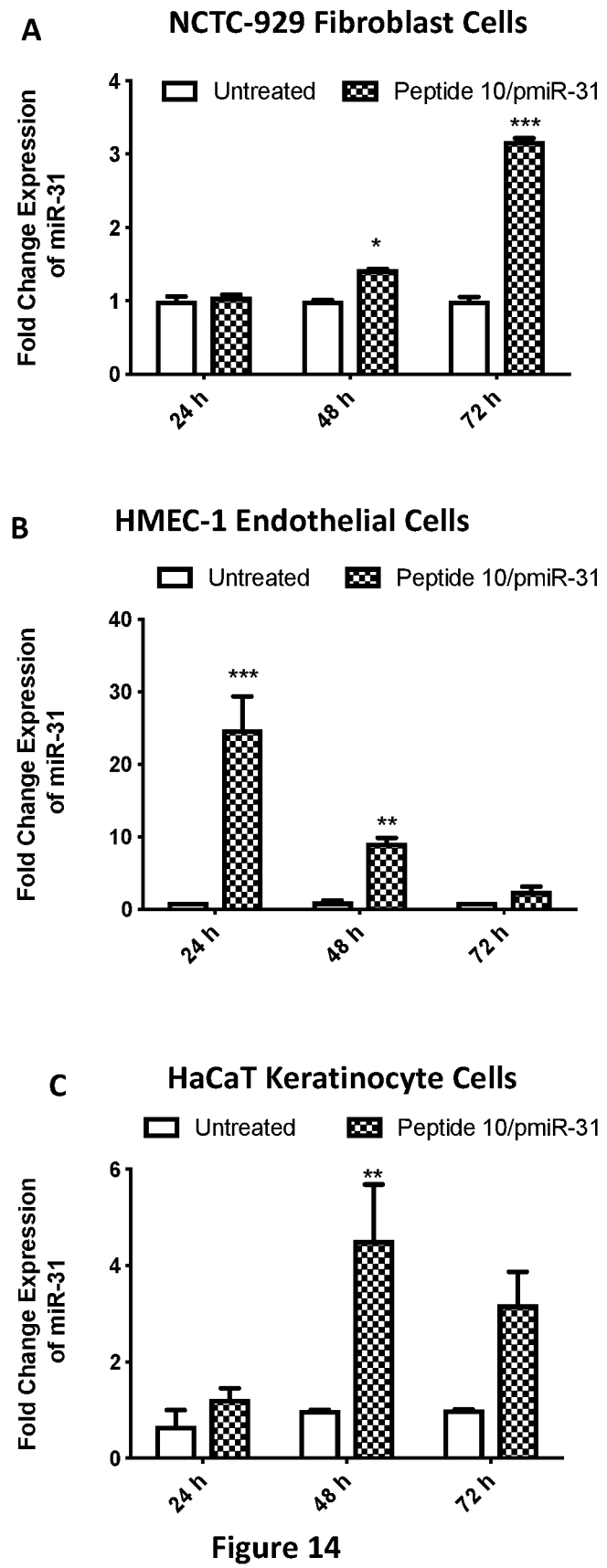

FIG. 14: Comparison of miR-31-fold change in expression in (A) NCTC-929 Fibroblast, (B) HMEC-1 Endothelial and (C) HaCaT Keratinocyte cells to assess the effect of Peptide 10/pmiR-31.) NCTC-929 Fibroblast, HMEC-1 Endothelial, and HaCaT Keratinocyte cells were transfected with 5 µg of pmiR-31 (Accession Number: MI0000089) at N:P ratios 10, 6, and 8 respectively in Opti-MEM in a 6-well plate and incubated at 37° C. in 5% $CO_2$. RNA was extracted from cell lines using mirVana (Invitrogen, UK). miR-31 and housekeeper, U6, were reverse transcribed and miR-31 expression relative to U6 quantified using qRT-PCR. Results are presented as fold change and reported as mean±SEM, n=3 (* p<0.05,  p<0.01, * p<0.001).

FIG. 15: Wound scratch assay in (A) NCTC-929 Fibroblast, (B) HMEC-1 Endothelial and (C) HaCaT Keratinocyte cells was performed to assess the effect of Peptide 10/pmiR-31 on cell migration. NCTC-929 Fibroblast, HMEC-1 Endothelial, and HaCaT Keratinocyte cells were transfected with Peptide 10/pmiR-31 or Peptide 10/pEGFP-N1 containing 5 µg of pDNA at N:P ratios 10, 6, and 8 respectively in Opti-MEM in a 6-well plate and incubated at 37° C. in 5% $CO_2$. 24, 48 and 72 h post-transfected cells were transferred to wound scratch assay inserts (Ibidi, UK) and wounded the following day for migration monitoring. Images were analysed using ImageJ software and the rate of migration relative to untreated control determined by comparing the area of each wound at the specified time points. Data is reported as mean±SEM, n=3 (*, p-value<0.05; **, p-value<0.01).

Figure 16:
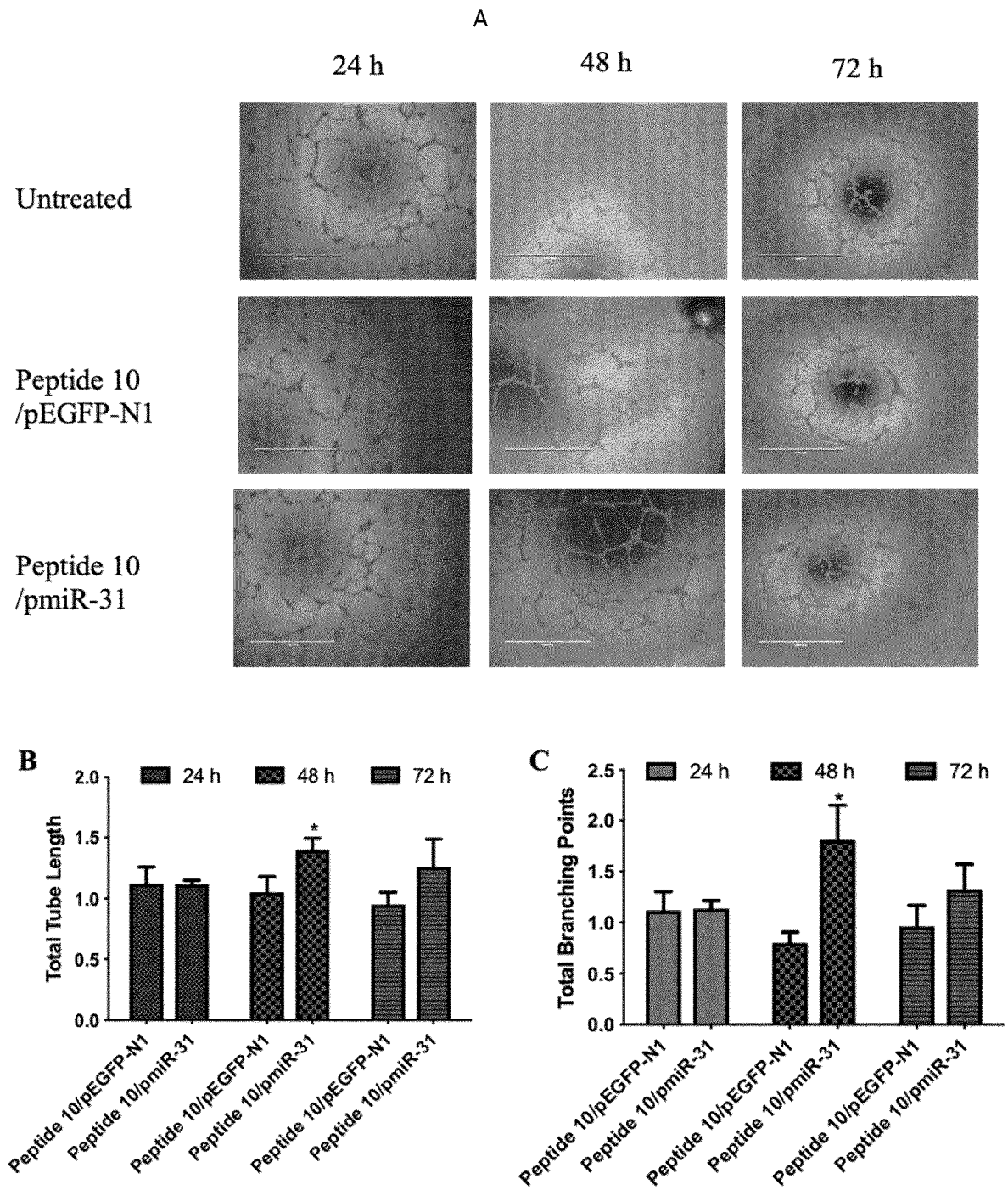

FIG. 16: Effect of Peptide 10/pmiR-31 on angiogenesis in HMEC-1 Endothelial cells at 24 h, 48 h and 72 h (FIG. 16A). Cells were transfected with Peptide 10/pmiR-31 or Peptide 10/pEGFP-N1 containing 5 µg of pDNA at N:P ratio 6. At each time point, cells were re-seeded onto Matrigel in triplicate in 96 well plates at a density of 20,000 per well in serum-free conditions. Total tubule length (FIG. 16B) and branching density (FIG. 16C) were measured using the WimTube software package. Data is reported as mean±SEM, n=3. (* p<0.05).

FIG. 17: (A) Schematic representation of the process of electrospinning. PVA polymer was weighed before being dissolved in $ddH_2O$ and then loaded into a syringe. The syringe was then loaded into the elctrospinning apparatus (SprayBase, Ireland) and nanofibres produced. Post-electrospinning, the PVA fibres were crosslinked with glutaraldehyde to confer stability and allow the loading of Peptide 10/pDNA nanoparticles through soak loading. (B) Gel retardation assay of Peptide 10/pDNA nanoparticles from electrospun PVA nanofibers incorporated post-electrospinning. The gel was prepared using agarose gel (1% w/v and 0.25 µg/mL etBr) with electrophoresis showing the mobility of pEGFP-N1 when dissociated from Peptide 10/pEGFP-N1 NPs ("released NPs+SDS"). Result images representative of three independent runs.

Figure 18:
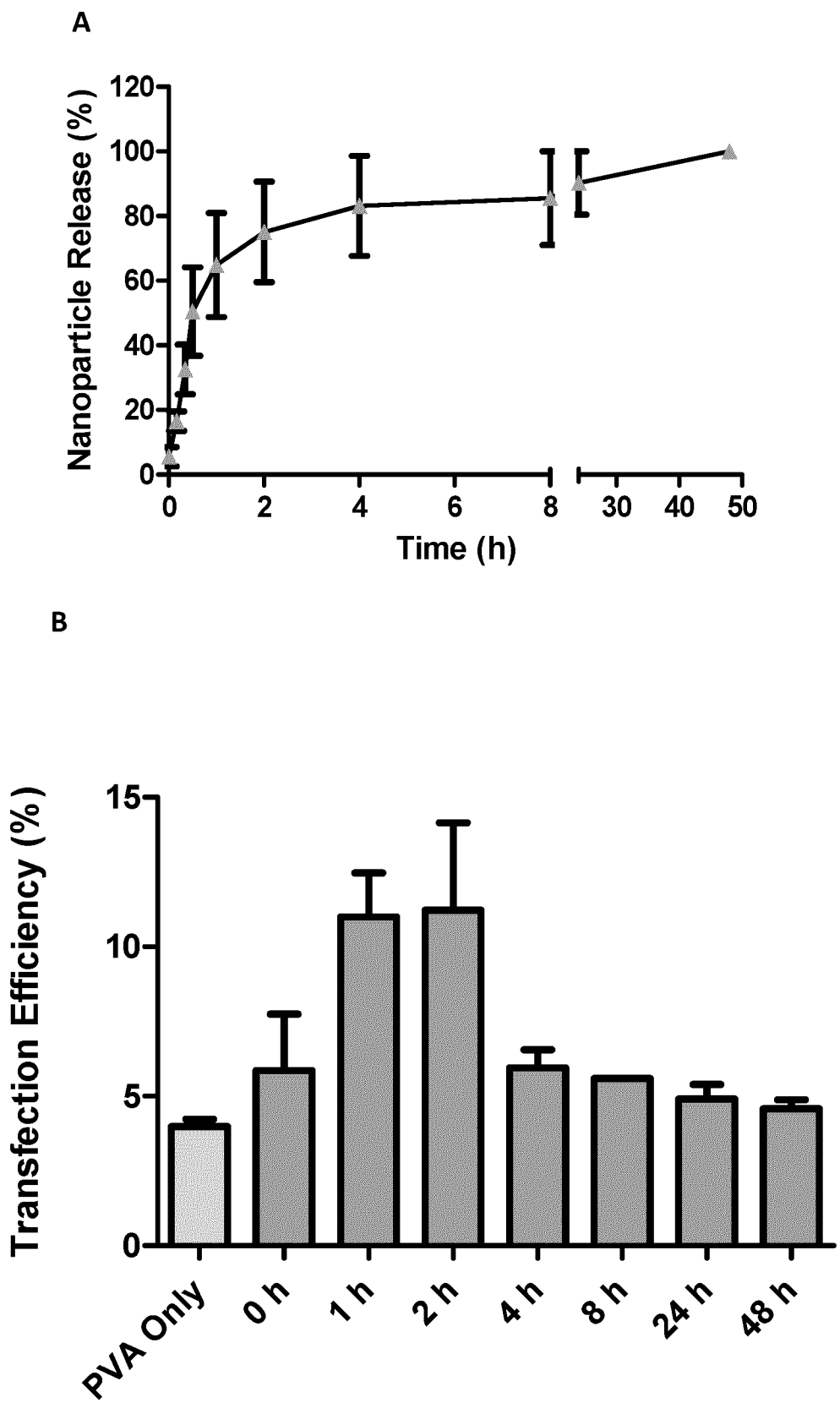

FIG. 18: Release and transfection profiles of Peptide 10/pEGFP-N1 nanoparticles released from crosslinked PVA nanofibres. (A) nanoparticle release with time up to 48 h, from a crosslinked PVA electro-spun patch, loaded with 10 µg of pEGFP-N1 complexed with Peptide 10. The patch was placed in 5 mL of Ultra Pure Water (Gibco, UK) and 200 µL samples taken at different time points. Samples were then treated with a proteinase-k enzyme to release the pDNA for quantification using the PicoGreen® assay. (B) shows the transfection of NCTC-929 Fibroblast cells with Peptide 10/pEGFP-N1 nanoparticles released between the different time points, confirming functionality post-release. Results displayed as mean±SEM, n=3.

Figure 19:
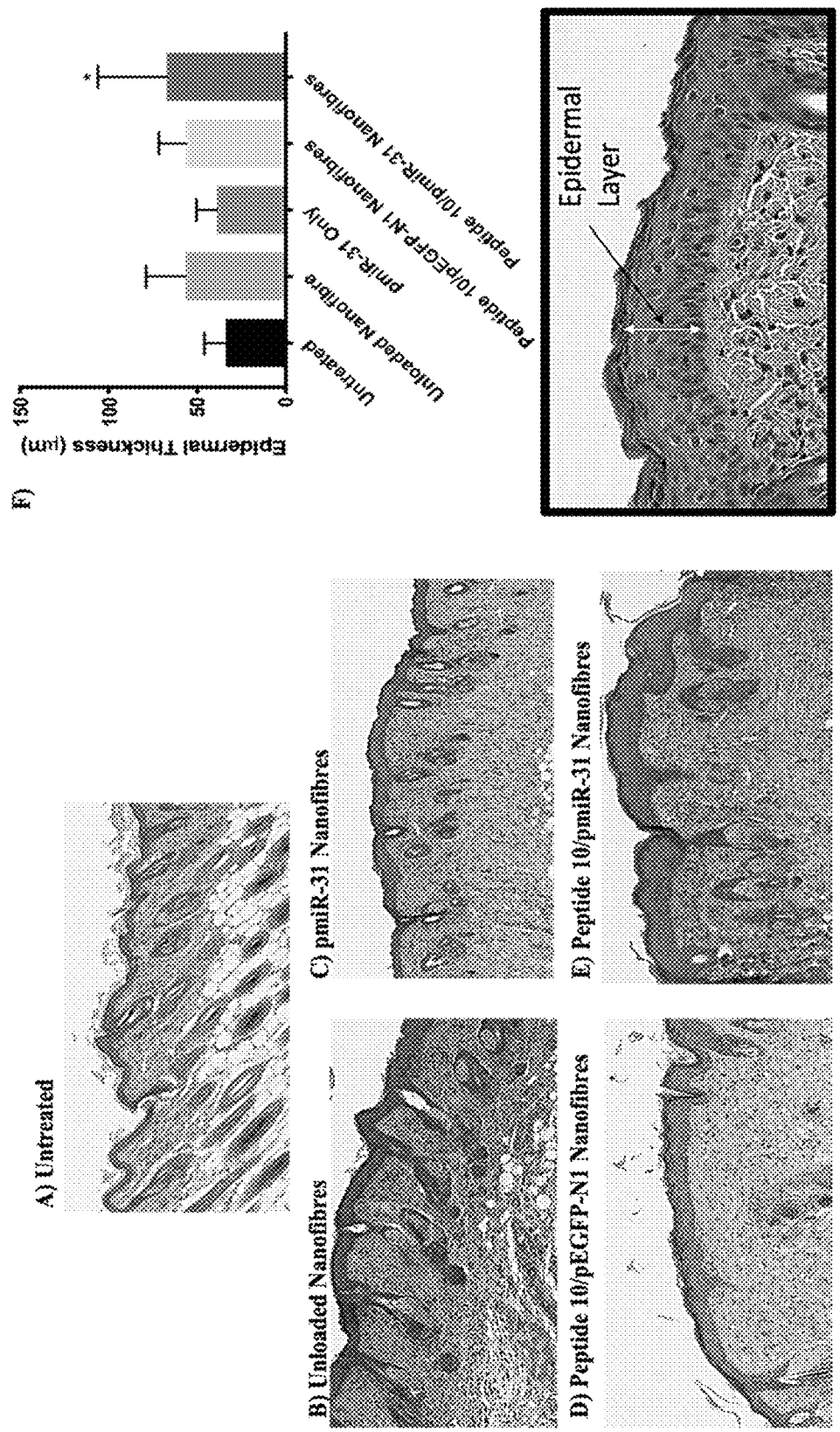

FIG. 19: The effects of treatments on the thickness of the epidermis in mice skin. After the C57BL/6N mice were euthanised at day 7, wound beds were harvested and fixed in 10% formalin for 24 h before pathologic examination. The tissue sections were embedded in paraffin and then cut into sections of thickness 3 µm and placed on glass microscope slides by the NIBioBank. The samples were processed for Hematoxylin and Eosin (H&E) staining. ImageJ analysis software (NIH) was then utilised for quantification of the epidermal thickness for each of the treatment groups: A) untreated, B) Unloaded Nanofibres, C) pmiR-31 Nanofibres, D) Peptide 10/pEGFP-N1 Nanofibres, and E) Peptide 10/pmiR-31 Nanofibres. The quantification of epidermal thickness in F). Data is reported as mean±SEM, n=5. (* $p<0.05$).

Figure 20:
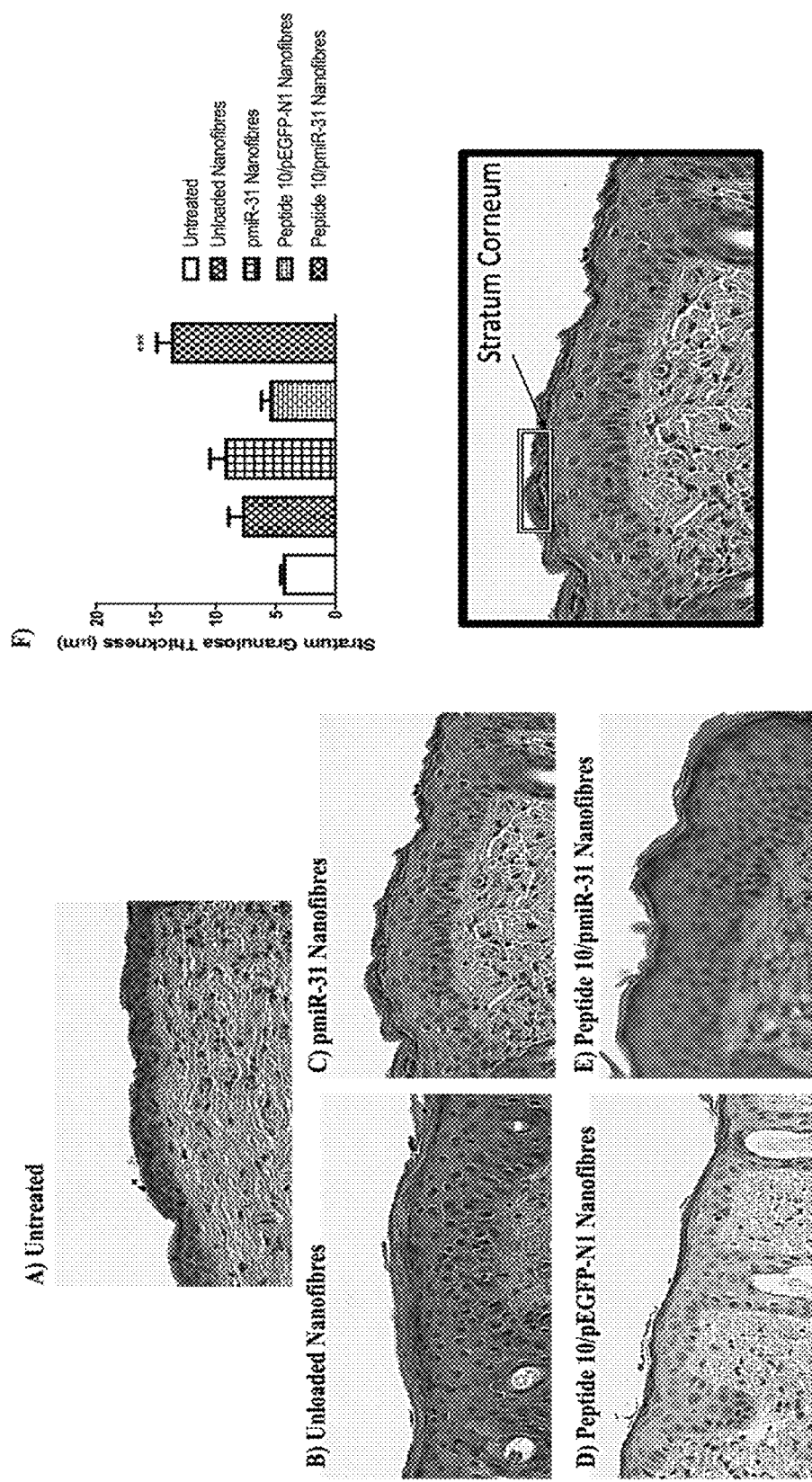

FIG. 20: The effects of treatments on the thickness of the stratum corneum (outer most layer) in mice skin. After the C57BL/6N mice were euthanised at day 7, wound beds were harvested and fixed in 10% formalin for 24 h before pathologic examination. The tissue sections were embedded in paraffin and then cut into sections of thickness 3 µm and placed on glass microscope slides by the NIBioBank. The samples were processed for Hematoxylin and Eosin (H&E) staining. ImageJ analysis software (NIH) was then utilised for quantification of the stratum corneum thickness for each of the treatment groups: A) untreated, B) Unloaded Nanofibres, C) pmiR-31 Nanofibres, D) Peptide 10/pEGFP-N1 Nanofibres, and E) Peptide 10/pmiR-31 Nanofibres. The thicknesses are represented in (F). Data is reported as mean±SEM, n=5. (*** $p<0.001$).

Figure 21:
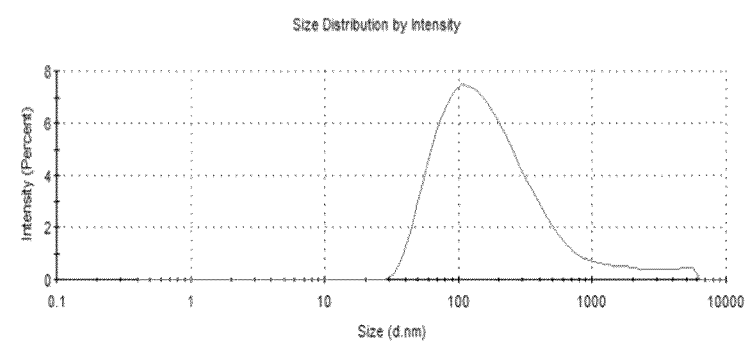
Figure 21:
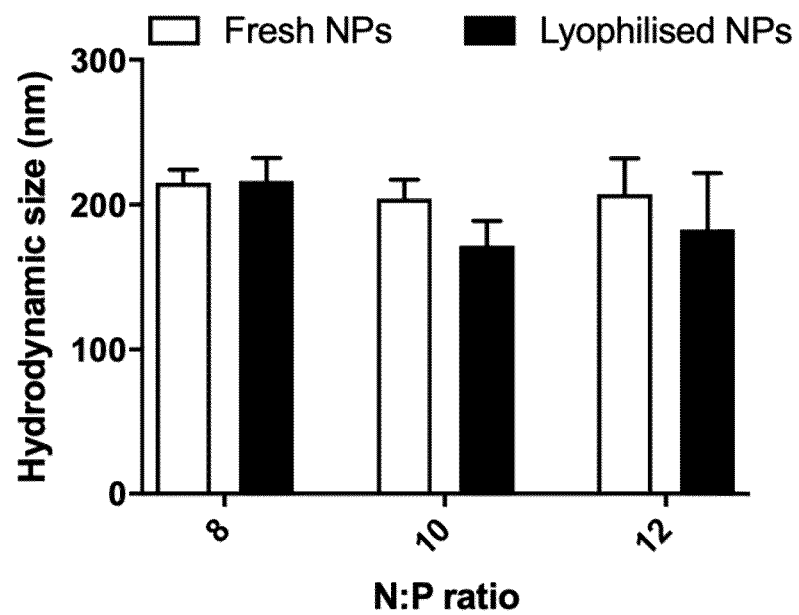

FIG. 21: Lyophilisation of Peptide 10/pDNA NPs. A) Size distribution of lyophilised Peptide 10/pDNA at N:P10. Peptide 10/pDNA complexes were prepared at N:P ratio of 10 and transferred into a glass lyophilisation vial in presence of the cryoprotectant Trehalose (5% final concentration) and frozen at −40° C. for 1 h. Subsequently the samples were subjected to primary drying at −40° C. and 60 mTorr for 24 h and a secondary drying program of −30° C. and 120 mTorr for 3 h, −30° C. and 190 mTorr for 3 h, −25° C. and 190 mTorr for 3 h and 20° C. and 190 mTorr for 6 h. Lyophilised Peptide 10/pDNA complexes were subsequently resuspended and hydrodynamic size and zeta potential were measured using a Malvern Zetasizer Nano ZS instrument. B) Comparison of hydrodynamic size of freshly prepared and lyophilised Peptide 10/pDNA at N:P 8, 10 and 10. Results are displayed as mean±SEM, n=3.

Figure 22:
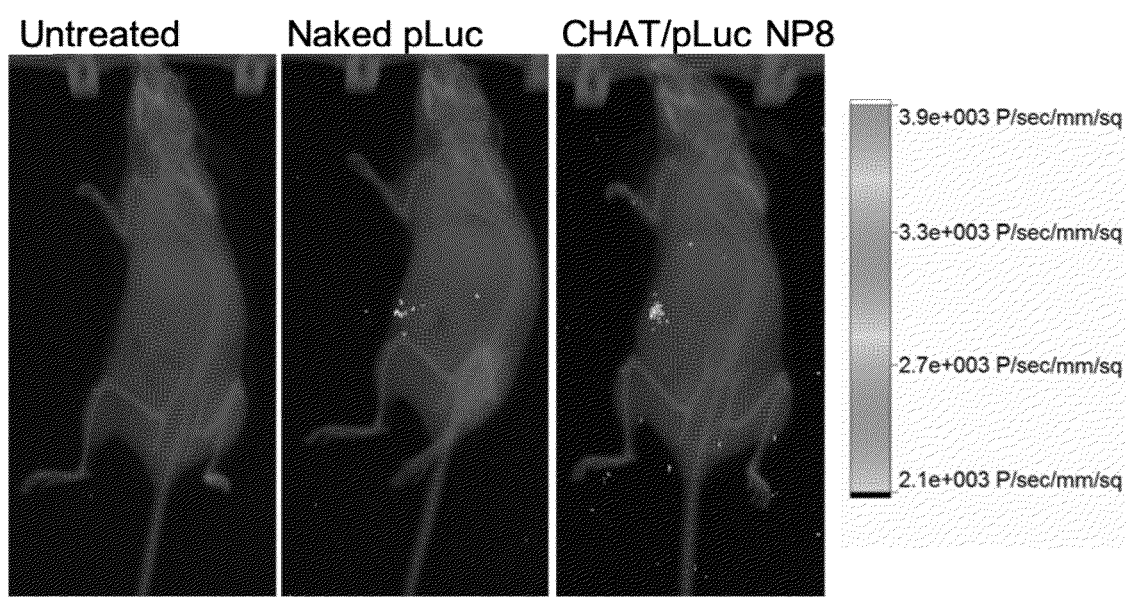

FIG. 22: In Vivo luciferase tissue distribution 24 h following intra-tumoural administration of Peptide 10/pLuc complexes to mice bearing 4T1 breast cancer tumours. Peptide 10/pLuc complexes were prepared at N:P 8 with 20 µg pLuc, lyophilised and reconstituted in 100 µl. Representative bioluminescent images captured using a Bruker InVivo Xtreme instrument.

MATERIALS AND METHODS

Generation of Peptides

All peptides were produced by solid state synthesis (FMOC chemistry) (Biomatik, Canada) and supplied as a lyophilised powder which required reconstitution before use. Peptides were supplied in the acetate salt form and were of >95% purity.

Plasmid DNA (pDNA)

pEGFP-N1 was purchased from Clontech (USA) (Accession Number: U55762.1), pmiR-31 was purchased from Origene (USA) (Accession Number: MI0000089), and pCMV-Red Fire-fly Luc (pLuc) was purchased from Oxford Genetics (UK) (SEQ ID NO:12). Plasmids were propagated in MAX Efficiency® DH5α™ Competent Cells (Life Technologies, UK), purified using PureLink®HiPure Plasmid Filter Maxiprep Kit (Life Technologies, UK) and quantified by UV absorption at 260 nm.

Cell Lines

MCF-7 and MDA-MB-231 breast cancer cells and HaCaT keratinocyte cells (ATCC, Manassas, VA) were maintained as monolayers in Dulbecco's Modified Eagle's Medium (DMEM) (Invitrogen, UK) supplemented with 10% foetal calf serum (FCS). MCF-10A non-tumourigenic mammary epithelial cells were maintained in phenol red free DMEM/F12 (Invitrogen, UK) supplemented with 5% horse serum (Invitrogen, UK), 20 ng/ml EGF (Thermofisher Scientific, UK), 0.5 mg/ml hydrocortisone (Sigma, UK), 100 ng/ml cholera toxin (Sigma, UK), 10 µg/ml insulin (Sigma, UK) and Pen/Strep (Invitrogen, UK). DU145 and PC-3 prostate cancer cells, and PNT2C2 non-tumourigenic prostate epithelial cells were maintained as monolayers in Roswell Park Memorial Institute medium (RPMI) supplemented with 10% FCS. NCTC-929 fibroblast cells (ATCC, Manassas, VA) were maintained as monolayers in Minimum Essential Medium (MEM) (Gibco, UK) supplemented with 10% foetal horse serum (FHS). HMEC-1 endothelial cells were maintained in MCDB-131 medium (ThermoFisher, UK) and supplemented with 5 µL Epidermal Growth Factor (EGF) (ThermoFisher, UK), 5 µL of 0.5 mg/ml hydrocortisone (Sigma, UK), 5 mL glutamine (ThermoFisher, UK), 5 Ml Pen/Strep (Invitrogen, UK) and 10% Fetal Bovine Serum (FBS).

When cells reached approximately 80% confluency, they were passaged and were not used for experimental protocols beyond a passage number of 20. Cells were maintained in an incubator at 37° C. with 5% $CO_2$ atmosphere and subjected to *mycoplasma* testing routinely. All in vitro cell experiments were carried out at 37° C. in a 5% $CO_2$ incubator. All cell lines were authenticated by short tandem repeat (STR) profiling carried out by the suppliers.

Animals

BALB/c SCID and C57BL/6N mice were purchased from Charles River Laboratories. The animals were housed in an open facility at 21° C. and 50% humidity with food and water ad libitum. The experimental protocols were compliant with the UK Scientific Act of 1986 and covered by the Department of Health, Social Services and Public Safety project license number 2794 and personal license number 1635.

Reconstitution of Peptides

Lyophilised peptides (Biomatik, Canada) were reconstituted in molecular grade water (Invitrogen, UK) and stored in aliquots at −20° C.

N:P Ratio Calculation for Peptide/DNA Nanoparticles

N:P ratio is widely used to describe the contents of peptide-/protein-based nucleic acid nanoparticles. It is defined as the molar ratio of positively charged nitrogen atoms in the amino acids of the peptide/protein to the negatively charged phosphates within the nucleic acid backbone or, more simply, the mass of peptide required to neutralise 1 µg of pDNA. N:P ratio can be calculated as follows:

$$N{:}P \text{ ratio} = \frac{M_{PROTEIN}}{M_{DNA}C_{NP}}.$$

where $M_{PROTEIN}$ is the mass of the peptide/protein in the nanoparticle, $M_{DNA}$ is the mass of the DNA in the nanoparticle and $C_{NP}$ is the N:P constant. The N:P constant is the ratio of the positive charge density of the amino acid chain to the negative charge density of the DNA, where charge density can be calculated as the charge divided by the molecular mass.

Based on the presence of the positively charged amino acids (mainly arginine and lysine) and the knowledge that the mass and charge of the bases in the DNA backbone are constant, the N:P constant can be calculated with only the mass and the charge of the peptide/protein as variables. $C_{NP}$ is calculated as follows:

$$C_{NP} = \frac{M_{PROTEIN}}{1\mu g_{DNA}NP} = \frac{Q_{DNA}MW_{DNA}}{Q_{PROTEIN}MW_{PROTEIN}} = \frac{Q_{DNA}MW_{PROTEIN}}{Q_{PROTEIN}MW_{DNA}} = \frac{2MW_{PROTEIN}}{650Q_{PROTEIN}}$$

which can be simplified to:

$$C_{NP} = \frac{2MW_{PROTEIN}}{650Q_{PROTEIN}}$$

For example, this can be calculated for Peptide 10 as follows:

$$C_{NP} = \frac{\text{No. of strands in } dsDNA \times MW \text{ Peptide 10}}{AvMW 1\mu g\, DNA \times \text{Charge Peptide 10}} = \frac{2 \times 2170}{650 \times 6} = 1.11$$

The $C_{NP}$ for each peptide is listed in Table 6 which was calculated from the molecular mass and charge of each.

TABLE 6

N:P ratio calculated for each of Peptides 7 to 12.

| Peptide | Peptide sequence | MW (Da) | Net Positive Charge | $C_{NP}$ |
|---|---|---|---|---|
| 7 | CRRRWHHHHHWRRRC | 2219.5 | 6 | 1.14 |
| 8 | CWRRRHHHHHRRRWC | 2219.5 | 6 | 1.14 |
| 9 | CHRHRHRWHRHRHRC | 2170.4 | 6 | 1.11 |
| 10 | CHHHRRRWRRRHHHC | 2170.4 | 6 | 1.11 |
| 11 | CRRRRWRRRRC | 1660 | 8 | 0.64 |
| 12 | CEHHRRRWRRRHHEC | 2154 | 6 | 1.10 |

Preparation of Cultured pDNA

A PureLink HiPure Plasmid Maxiprep kit (Invitrogen, UK) was used to purify pEGFP-N1, pLuc and pmiR-31 for determination of peptide/pDNA interaction. 200 ml of LB broth containing 50 µg/ml kanamycin for pEGFP-N1, 100 µg/ml ampicillin for pLuc or 50 µg/ml kanamycin for pmiR-31 was inoculated with 1 ml glycerol stock of Max Efficiency DH5a competent cells (Life Technologies) transformed with pEGFP-N1 or pLuc and incubated overnight at 37° C. in an orbital incubator. Bacterial cells were then harvested by centrifugation at 4000 g for 15 min at 4° C. Buffers supplied in the kit were used to lyse the bacterial pellet and precipitate out any proteins. The pDNA was purified using anion exchange resins provided in the kit, precipitated with isopropanol (Sigma-Aldrich, UK), air dried and resuspended in molecular grade water (Invitrogen, UK). The concentration of purified pDNA was determined by UV spectrophotometry using a Nanodrop 2000 spectrophotometer (ThermoScientific, USA) at a wavelength of 260 nm, and purity was determined by A260/280 determination.

Formulation of Peptide/pEGFP-N1. pLuc or pmiR31 Nanoparticles

Plasmid DNA was complexed by each peptide according to a range of N:P ratios via electrostatic interactions. According to the N:P ratio, a quantity of peptide was added to 1 µg of pDNA in aqueous solution and the final volume was adjusted to 50 µl with molecular grade water. The samples were then incubated at room temperature for 30 min. Formulation of nanoparticles prepared for linear peptides in Table 7.

TABLE 7

Components of nanoparticles formed at N:P ratio 10 for each of Peptides 7 to 12.

| Peptide | Mass DNA (µg) | Mass of peptide for N:P 1 (µg) | Mass of peptide for N:P 10 (µg) | Volume $H_2O$ (µl) |
|---|---|---|---|---|
| 7 | 1 | 1.14 | 11.4 | to 50 µl |
| 8 | 1 | 1.14 | 11.4 | to 50 µl |
| 9 | 1 | 1.11 | 11.1 | to 50 µl |
| 10 | 1 | 1.11 | 11.1 | to 50 µl |
| 11 | 1 | 0.64 | 6.4 | to 50 µl |
| 12 | 1 | 1.10 | 11.0 | to 50 µl |

For example, at an N:P ratio of 10, 11.4 µg of Peptide 7 is added to 1 µg of pEGFP-N1 in aqueous solution, the final volume adjusted to 50 µl with water and left to incubate for 30 min at room temperature.

Densitometry of Gel Electrophoresis Assay Fluorescence—FIG. 1

DNA that remains at original ("well", herein) is uncharged. For Peptides 7 and 12, this is achieved at an N:P ratio of 6 to 20. For Peptides 8, 9, 10, and 11, this is achieved at an N:P ratio of 4 to 20.

Complexation of pDNA—FIG. 2

Peptide complexes and composite complexes were prepared at a range of N:P ratios from 1 to 20 to complex 0.5 µg pEGFP-N1. Quant-iT™ PicoGreen® Reagent (Life Technologies, UK) was diluted 1:200 in TAE buffer and 50 µl was added to each 50 µl sample. Sample fluorescence was analysed by excitation at 480 nm and the fluorescence emission intensity measured at 520 nm using a Synergy 2 Multi-Mode Plate Reader. Fluorescence intensity of a naked pDNA control (an N:P ratio of 0) was taken as 100% fluorescence and 0% complexed, and any fluorescence detected from samples was taken to be un-complexed. The percentage of un-complexed pDNA in each sample was then used to calculate the percentage of complexed pDNA.

FIGS. 1 and 2 illustrate overall charge (FIG. 1) and % encapsulation (FIG. 2) of the various composite complexes. Both an overall neutral charge and >70% encapsulation are observed at an N:P ratio of 6 to 20 for each of Peptides 7, 8, and 11. An overall neutral charge and >70% encapsulation is observed at an N:P ratio of 4 to 20 for Peptide 10 of the present invention.

Nanoparticle Size Measurement using Malvern Zetasizer—FIG. 3

Peptide complexes (an N:P ratio of 0) and composite complexes were prepared at a range of N:P ratios from 1 to 20 to complex 0.5 µg pEGFP-N1. For example, at an N:P ratio of 10 with Peptide 7, nanoparticles comprise 0.5 µg of pEGFP-N1 and 5.7 µg Peptide 7. Nanoparticles were made up to 50 µl with molecular grade water and incubated for 30 min at room temperature before a Malvern Zetasizer Nano ZS instrument with DTS software (Malvern Instruments, UK) was used to measure the mean hydrodynamic particle size of nanoparticles. A 40 µl disposable microcuvette was used to measure the mean size by number of nanoparticles formed by Dynamic Light Scattering (DLS) at 20° C. Results were reported as mean±SEM, and all measurements were performed in triplicate.

A hydrodynamic size of <200 nm is preferred. All of peptides 7 to 12 have a hydrodynamic size of <200 nm at an N:P ratio of 6 to 20. Peptide 10 of the present invention is associated with a hydrodynamic size of <150 nm at an N:P ratio of 6 to 20.

Determination of Nanoparticle Zeta Potential using Malvern Zetasizer—FIG. 3

Following size measurement, 50 µl of the nanoparticles sample was subsequently diluted to 1000 µl with molecular grade water and added to a folded capillary zeta cell (Malvern Instruments, UK). Zeta potential was measured by Laser Doppler Velocimetry using a Malvern Zetasizer Nano ZS instrument with DTS software at 20° C. Results were reported as mean±SEM, and measured in triplicate.

A Zeta Potential in the range of 10 to 35 mV is preferred. Peptides 7 to 12 exhibit a Zeta Potential in the range of 10 to 35 mV at an N:P ratio of 8 to 20.

Determination of Polydispersity Index (PDI) and Particle Count (Kilocounts Per Second) Using Malvern Zetasizer—FIG. 4

Polydispersity index (PDI) and particle count (kilocounts per second) of nanoparticles prepared with pEGFP-N1 and A) Peptide 7, B) Peptide 8, C) Peptide 8, D) Peptide 10, E) Peptide 11 or F) Peptide 12 at a range of N:P ratios corresponding to size and zeta potential analysis in FIG. 3. Nanoparticles were made up to 50 µl with molecular grade water and incubated for 30 min at room temperature before PDI and particle count were measured using a Malvern Zetasizer Nano ZS instrument. Results are displayed as mean±SEM, n=3.

A polydiversity index of 0.15 to 0.4 is preferred. Peptides 7 to 10 exhibit a polydiversity index in the range of 0.15 to 0.40 at an N:P ratio of 4 to 20. Peptide 10 of the present invention exhibits a polydiversity index in the range of 0.25 to 0.35 at an N:P ratio of 4 to 20.

A particle count of 100 to 200 is preferred. Peptides 7 to 10 exhibit a particle count of 100 to 200 at an N:P ratio of 4 to 20. Peptide 10 of the present invention exhibits a particle count in the range of 100 to 150 at an N:P ratio of 4 to 20.

Transfection with Peptide Delivering pEGFP-N1—FIGS. 5, 10, 12

In order to assess the ability of peptide and composite nanoparticles to transfect cells, transfections were carried out in 96-well tissue culture plates.

MCF-7 and MDA-MB-231 breast cancer cells were seeded at a density of $2.25 \times 10^4$ and $2.5 \times 10^4$ cells per well respectively, and allowed to adhere overnight at 37° C. with 5% $CO_2$ (FIG. 5).

PC-3 and DU145 prostate cancer cells were seeded at a density of $2.5 \times 10^4$ and $2 \times 10^4$ cells per well respectively, and allowed to adhere overnight at 37° C. with 5% $CO_2$ (FIG. 10).

NCTC-929, HMEC-1, and HaCaT cells were seeded at a density of $1.75 \times 10^4$ and $2 \times 10^4$ and $1.7 \times 10^4$ cells per well respectively, and allowed to adhere overnight at 37° C. with 5% $CO_2$ (FIG. 10). ARPE cells were seeded at a density of $20 \times 10^3$ cells per well, and allowed to adhere overnight at 37° C. with 5% $CO_2$ (FIG. 12).

Medium was replaced with OptiMEM (Invitrogen, UK) 2 h prior to transfection and the cells returned to the incubator at 37° C. with 5% $CO_2$. Nanoparticles containing 0.5 µg pEGFP-N1 were prepared at a range of N:P ratios in a total volume of 50 µl before being added to the appropriate wells.

Cells were incubated with the nanoparticles for 4 h, before being replaced with complete media. Untreated cells and cells treated with naked pDNA served as negative controls.

In FIG. 10, DU145 and PC-3 prostate cancer cells were transfected for 4 h with Peptide 10/pEGFP-N1 nanoparticles at N:P ratios in the range of 6 to 20.

In FIG. 10, NCTC-929 Fibroblast, HMEC-1 Endothelial and HaCaT Keratinocyte cells were transfected with Peptide 10/pEGFP-N1 for 4 h with nanoparticles at a range of N:P ratios in the range of 6 to 20.

FIG. 5 compares the % transfection, in MCF-7 cells and MDA-MB-231 cells, for each of Peptides 7 to 12.

A % transfection is >10% is preferred. Peptide 10 is associated with >15% transfection, in both cell lines, at N:P ratios of 6 to 20 (see FIG. 5). Peptide 12 is associated with >10% transfection, in both cell lines, at N:P ratios of 6 to 10 (see FIG. 5).

FIG. 10 compares the transfection efficiency of nanoparticles comprising pEGFP-N1 and Peptide assessed in DU145 and PC-3 prostate cancer cells, NCTC-929 fibroblast, D) HMEC-1 endothelial, and E) HaCaT keratinocyte cells. Peptide 10 is associated with >10% transfection, in all 5 cell lines, at N:P ratios of 6 to 20 (see FIG. 10).

FIG. 12 illustrates the transfection efficiency and cell viability of nanoparticles comprising pEGFP-N1 and Peptide 10 in ARPE human retinal cells. Peptide 10 is associated with >10% transfection, in all 5 cell lines, at N:P ratios of 8 to 12 (see FIG. 12).

Endosomal Escape and Cellular Uptake Pathway Studies—FIG. 6

In some instances, cells were treated with chloroquine (a reagent known to facilitate endosomal escape) (FIG. 6). For endosomal escape studies, 1 mM chloroquine (Sigma-Aldrich, UK) was added to the cells immediately before transfection, giving a final concentration of 10 µM chloroquine in the nanoparticle transfection mix.

FIG. 6 compares the transfection efficiency of nanoparticles comprising pEGFP-N1 and Peptides 7 to 12 assessed in MCF-7 and MDA-MB-231 breast cancer cells with and without chloroquine. In MCF-7 cells, Peptides 10 to 12 are associated with a smaller increase in % transfection, in the presence of chloroquine. In MDA-MB-231 cells, all of Peptides 7 to 12 are associated with an increase in % transfection, in the presence of chloroquine.

Fluorescence Microscopy

To facilitate qualitative analysis of pEGFP-N1 expression correlating to transfection efficiency, cells were visualised and imaged 48 h following transfection under fluorescent light using an EVES FL Cell Imaging System (Life Technologies).

Flow Cytometry Analysis of Transfection Efficiency—FIGS. 5, 10, 12

Transfected cells were washed with phosphate buffered saline (PBS) and 2× trypsin used to detach cells at 37° C. in 5% $CO_2$ atmosphere. Complete media was then added and the cells were centrifuged at 2300 g for 10 min. The cell pellet was subsequently resuspended in 2% formaldehyde in PBS and kept refrigerated at 4° C. until analysis. A FACScalibur system (BD Bioscience, UK) or Accuri C6 Plus (BD Bioscience, UK) were used for the detection of green fluorescent protein (GFP) expressing cells at 4% gating (to reduce interference of auto-fluorescence) and results are reported as mean±SEM, n=3.

Microscopic Analysis of Intracellular Delivery of pDNA—FIG. 9 pDNA was fluorescently labelled with the Cy3 fluorophore (Mirus, USA) according to manufacturer's instructions. MDA-MB-231 and PC-3 cells were seeded at $4 \times 10^4$ per well onto the surface of a coverslip in a 24-well plate and allowed to adhere overnight. Cells were then transfected with nanoparticles as described in section 0. 30 min, 2 h and 4 h post transfection cells were fixed and permeabilised with 4% formaldehyde and 0.1% Triton-X (Sigma, UK) for 20 min. Cells were then stained with Fluorescein (FITC)-phalloidin (Life technologies, UK) at room temperature for 15 min and mounted onto a microscope slide with Fluoroshield mounting medium containing DAPI nuclear stain (Life Technologies, UK). Cells were then imaged using a CytoViva Hyperspectral microscope (CytoViva, USA) and a TSC SP5-Leica Microsystems confocal microscope (Leica, UK) and analysed using LAS AF Lite Software (Leica, UK).

The confocal microscopy images illustrate nuclear delivery of Peptide 10 of the present invention at N:P 12 delivering Cy3 labelled pDNA into MDA-MB-231 breast cancer cells.

Cell Viability—FIGS. 11 and 12B

Cell viability was evaluated by MTS assay with CellTiter 96 AQueous One Solution Cell Proliferation Assay (Promega, UK). MDA-MB-231 and PC-3 cells were seeded at a density of $1.5 \times 10^4$ cells per well and MCF-7, and DU145cells seeded at $1.2 \times 10^4$ cells per well, ARPE, NCTC-929, HMEC-1, and HaCaT cells seeded at $1.0 \times 10^4$, and allowed to adhere in a 96 well plate. Cells were transfected CellTiter reagent was added to each well 24 h post transfection to give a final volume of 10% and returned to the incubator for 2 h. Absorbance was read at 490 nm using a Bio-Tek Powerwave XS plate reader with Gen5 software and any background absorbance was subtracted from readings. Cell viability was expressed as a percentage of the untreated control where the untreated control is considered to be 100% viable.

FIG. 12B illustrates that cell viability decreases as the N:P ratio is increased.

>60% cell viability is desired. >60% cell viability is achieved for Peptide 10 of the present invention at an N:P ratio of 6 to 15, such as an N:P ratio of 6 to 12.

Temperature Stability—FIG. 8

Peptide and composite complexes were prepared. Particle size was measured at various temperatures using a Nano ZS Zetasizer with DTS software (Malvern Instruments, UK).

The mean hydrodynamic size of Peptide 10/pEGFP-N1 nanoparticles was determined to assess stability across a temperature range of 4 to 40° C. Peptide 10/pEGFP-N1 nanoparticles are stable over the temperatures assessed. The hydrodynamic size varies between 75 and 200 nm over the temperatures tested.

The polydispersity index varied between 0.3 and 0.55 over the temperatures tested. The KCPS varies between 150 and 400 over the temperatures tested.

Stability Over Time—FIG. 7

Peptide and composite complexes were prepared. Complexes were stored at room temperature for up to one month in Eppendorf tubes. At the indicated time points, particle size and zeta potential were measured.

The mean hydrodynamic size of Peptide 10/pEGFP-N1 nanoparticles was determined to assess stability across a 12 h time period and a 28-day time period. Peptide 10/pEGFP-N1 nanoparticles are stable over both time periods. The hydrodynamic size varies between 75 and 200 nm over a 12 hour time period; and over a 28 day period. The Zeta Potential varies between 10 and 40 mV over a 28 day period.

Ex vivo luciferase tissue distribution 48 h following systemic administration of Peptide 10/pLuc complexes to mice bearing MDA-MB-231 xenografts—FIG. 13.

Peptide 10/pLuc complexes were prepared at N:P 8 with 50 µg pLuc. Complexes were subsequently administered to BALB/c SCID mice via tail vein injection in a total volume of 200 µl. Mice were sacrificed at 48 h post injection and organs harvested. Quantification of luciferase gene expression in the brain, lungs, liver, kidney, spleen, and tumour was analysed using qRT-PCR. Total mRNA was extracted from organs, reverse transcribed and luciferase expression relative to housekeeper (p-actin) analysed using qRT-PCR. Gene expression is expressed as fold difference relative to untreated control and points represent mean±SEM, n=3.

FIG. 13 illustrates increased luciferase expression in brain, lung, liver, kidney, spleen and tumour (the MDA-MB-231 xenograft).

Real-Time PCR of pmiR-31—FIG. 14

RNA was extracted by phase separation using a mirVana kit (Thermofisher Scientific, UK) according to the manufacturer's protocols. Purified RNA was eluted in 100 µL of DNase/RNase-free H2O (Gibco, UK) and stored at −20° C. until required. Reverse transcription reactions were conducted in polypropylene tubes according to manufacturer's protocol (TaqMan Small RNA assay, Invitrogen, UK). Reverse transcription master mix was prepared using 0.15 µL 100 mM dNTPs, 1 µL Multiscribe Reverse Transcriptase, 1.5 µL 10× Reverse transcription buffer, 0.19 µL RNase Inhibitor, 4.16 µL Nuclease-free $H_2O$ to give a final total volume of 7 µL/reaction. 5 µL of RNA sample (containing 10 ng of RNA) and 3 µL of 5XRT primer (miR-31 or U6) is then added to the relevant polypropylene tube to give a final reaction volume of 15 µL. Tubes were centrifuged for 5 seconds. Reverse transcription was conducted using a TC-312 thermocycler (Techne, UK). The incubation cycles were 16° C. for 30 min, 42° C. for 30 min, 85° C. for 5 min, hold at 4° C. qRT-PCR was conducted using transparent 96-well plates (Roche, UK). Reactions were prepared for each set of probes (miR-31 and U6) according to manufacturer's protocols (TaqMan Small RNA assay, Invitrogen, UK). Briefly, 0.5 µL of TaqMan Small RNA assay (20×); 5 µL of TaqMan Universal PCR Mastermix Mix II (2×), no UNG; 3.84 µL Nuclease-free $H_2O$; 0.67 µL cDNA (from RT reaction) were prepared to give a total reaction volume of 10 µL/well. qRT-PCR was conducted using a Lightcycler 480 II (Roche, UK) using the following cycling parameters: 95° C.

for 10 min then 40×cycles of 95° C. for 15 s and 60° C. for 60 s. The Ct values generated were used to quantify miR-31 expression relative to U6 using the $\Delta\Delta C_T$ method. Results are reported as fold change relative to control. FIG. 14 compares miR-31-fold change in expression in NCTC-929 Fibroblast, HMEC-1 Endothelial and HaCaT Keratinocyte cells to assess the effect of Peptide 10/pmiR-31. In each cell line, Peptide 10/pmiR-31 increases expression of pmiR-31 at least at 48 hours post-transfection.

Wound Scratch Assay—FIG. 15

Wound scratch culture inserts (Ibidi, UK) were directly pipetted with either 70×10⁴ NCTC-929, HMEC-1, or HaCaT cells in a 24-well plate. Culture-inserts were gently removed with sterile tweezers 12 h after seeding, and the cell layer was washed with PBS. Then 1 mL of cell culture medium (2% FCS) placed into each well of the 24-well plate. Cells were imaged using an EVOS FL Cell Imaging System (Life Technologies) at different time points up until the untreated control had closed by 50%. Remaining wound area is presented as fold change normalised to untreated control. This assay has been used by many groups in order to assay cell functionality upon treatment. Below is a list of sample references which show this:

Grada, A., Otero-Vinas, M., Prieto-Castrillo, F., Obagi, Z., & Falanga, V. (2017). Research Techniques Made Simple: Analysis of Collective Cell Migration Using the Wound Healing Assay. Journal of Investigative Dermatology, 137(2), e11-e16. <https://doi.org/10.1016/J.JID.2016.11.020> Heikal, L., Ghezzi, P., Mengozzi, M., & Ferns, G. (2018). Assessment of HIF-1$a$ expression and release following endothelial injury in-vitro and in-vivo. Molecular Medicine, 24(1), 22. <https://doi.org/10.1186/s10020-018-0026-5>

Liang, C.-C., Park, A. Y., & Guan, J.-L. (2007). In vitro scratch assay: a convenient and inexpensive method for analysis of cell migration in vitro. Nature Protocols, 2(2), 329-333. <https:/doi.org/10.1038/nprot.2007.30>

FIG. 15 assesses the effect of Peptide 10/pmiR-31 on cell migration. In each cell line, Peptide 10/pmiR-31 reduces remaining wound area, when compared to Peptide 10/pEGFP-N1, at least at 48 hours post-transfection.

Tubule Formation Assay—FIG. 16

Matrigel (70 µL) (Corning, UK) was pipetted into a 96-well plate and left to incubate for 1 h at 37° C. HMEC-1 cells were grown in a monolayer and trypsinized before being suspended in serum-free media. Cells were counted and 2.5×10⁴ cells were pipetted onto the Matrigel. Cells were left overnight for a period of 14 h, allowing tubules to form. Tubules were imaged EVOS FL Cell Imaging System (Life Technologies), then total tube length, and total branching points were calculated using WimTube software (Wimasis Image Analysis, Munich, Germany). Results are presented as fold change normalised to untreated control. Peptide 10/pmiR-31 or Peptide 10/pEGFP-N1

FIG. 16 assesses the effect of Peptide 10/pmiR-31 on tubule formation. Peptide 10/pmiR-31 increases tubule formation, when compared to Peptide 10/pEGFP-N1, at least at 48 hours post-transfection.

Production of PVA Nanofibres—FIG. 17

Nanofibres of poly (vinyl alcohol) (PVA) MW 146-180 Kda (Sigma, UK) were manufactured via the electrospinning process (SprayBase, Ireland). Parameters for production included an applied voltage of 8 kV, a working distance of 8 cm, a polymer flow rate of 4 µL/min, and a polymer concentration of 9% w/v. Nanofibres were produced over a 2 h period then crosslinked with a 1% glutaraldehyde (Sigma, UK)/methanol(Sigma, UK) solution for 4 h. After crosslinking, the nanofibres were washed 3 times with methanol, followed by three washes with ultrapure water (Gibco, UK). Nanofibres were then air dried for 24 h. Nanofibres were then sterilised for 1 h under ultra-violet light.

Loading of Peptide 10/miR31 NPs into Nanofibres—FIG. 17

Nanoparticles of Peptide 10/pmiR-31 containing 10 µg were synthesised at N:P ratio 8 as described previously. Once synthesised, the nanoparticle solution was pipetted directly onto 1 cm by 1 cm sections of the sterilised crosslinked PVA nanofibres, and allowed to soak in and dry over a 24 h period.

The gel of FIG. 17B shows the mobility of pEGFP-N1 when dissociated from Peptide 10/pEGFP-N1 NPs ("released NPs+SDS"). The intact band similar to DNA shows that there was no damage to the released DNA from the PVA nanofibres.

Release of Peptide 10/miR31 NPs from nanofibres—FIG. 18

Electrospun nanofibres incorporating 10 µg of DNA NPs at N:P ratio 8 were placed in 5 mL ultrapure water (Gibco, UK) and samples taken at different time points up to 48 h. Samples were then incubated with Proteinase-K (Thermo-Scientific, UK) for 90 min at 37° C. to dissociated nanoparticles. DNA release was determined using the Quanti-iT™ Picogreen® assay (Life Technologies, UK).

FIG. 18A illustrates nanoparticle release with time up to 48 h, from a crosslinked PVA electro-spun patch, loaded with 10 µg of pEGFP-N1 complexed with Peptide 10. FIG. 18B shows the transfection of NCTC-929 Fibroblast cells with Peptide 10/pEGFP-N1 nanoparticles released between the different time points, confirming functionality post-release. Transfection efficiency is optimal 1 to 2 hours post administration of the electrospun nanofibres.

In vivo studies with Peptide 10/miR31 nanofibres—FIGS. 19 and 20

C57BL/6N mice were anaesthetised using Isoflurane before hair was removed from the dorsum initially by shaving with hair clippers then hair removal cream for complete removal. The surgical site is prepared by disinfection with 70% alcohol. Dorsal skin is folded and raised using index finger and thumb to create a skinfold. The mouse was placed in the lateral position, and a 5-mm diameter sterile disposable biopsy punches (Stiefel, UK) was used to completely remove two skin layers. This created symmetrical full thickness wounds. The day of surgery was considered day 0 of the experiment. After surgery, the wounds were treated with PVA nanofibers, PVA nanofibres loaded with nanoparticles containing 20 µg of pDNA at N:P ratio 8, and control dressing Durafiber@. A secondary dressing was placed over the wounds, consisting of a commercial transparent film Tegaderm™. After surgery animals were moved to a warm area and recovery from anaesthesia was monitored. Once fully recovered the animal was moved to routine housing and caged individually. At 7-days post-surgery the mice were euthanised and the wound beds were harvested.

Immunohistochemistry

After the mice were euthanised, wound beds were harvested and fixed in 10% formalin for 24 h before pathologic examination. The tissue sections were embedded in paraffin and then cut into sections of thickness 3 µm and placed on glass microscope slides by the NIBioBank. The samples were processed for Hematoxylin and Eosin (H&E) staining. Samples were then analysed in terms of epidermal thickness, blood vessel size and density, and the thickness of the stratum corneum.

Lyophilisation of Peptide 10/pDNA NPs—FIG. 21

Peptide 10/pDNA complexes were prepared at N:P ratio of 10 and transferred into a glass lyophilisation vial in presence of the cryoprotectant Trehalose (5% final concentration) and frozen at −40° C. for 1 h. Subsequently the samples were subjected to primary drying at −40° C. and 60 mTorr for 24 h and a secondary drying program of −30° C. and 120 mTorr for 3 h, −30° C. and 190 mTorr for 3 h, −25° C. and 190 mTorr for 3 h and 20° C. and 190 mTorr for 6 h. Lyophilised Peptide 10/pDNA complexes were subsequently resuspended and hydrodynamic size and zeta potential were measured using a Malvern Zetasizer Nano ZS instrument.

FIG. 21a shows a typical trace of lyophilised Peptide 10/pDNA nanoparticles. FIG. 21b compares the hydrodynamic size of fresh and lyophilised Peptide 10/pDNA nanoparticles with no significant difference across N:P ratios.

Local intratumoural delivery of Peptide 10/pDNA nanoparticles to subcutaneous 4T-1 tumours.

Peptide10/pDNA was delivered directly to the subcutaneous tumour of mice bearing 4T1 breast cancer xenografts. Peptide 10/pLuc complexes were prepared at N:P 8 with 20 µg pLuc, lyophilised and reconstituted in 100 µl of ddH$_2$O. Representative bioluminescent images captured using a Bruker InVivo Xtreme instrument.

FIG. 22 shows that Peptide 10 could be used to deliver pDNA locally into accessible tumours.

CONCLUSION

Several variant linear peptides were designed keeping the sequence length and composition similar but altering the position of histidine, arginine and tryptophan/alanine residues. The impact of peptide sequence variation on complex formation, cellular uptake, endosomal escape and overall transfection efficiency was analysed with the overall aim of a better understanding of peptide sequence on functionality.

Each of the linear peptides neutralised pDNA and, with increasing N:P ratio, the migration of pDNA through the agarose gel was impeded. The theoretical net charge of comparative Peptides 7, 8, 9 and Peptide 10 of the present invention was similar and there was minimal variation in neutralisation and complexation. Comparative Peptide 12 has a slightly different profile, with two anionic glutamic acid residues reducing the net charge of the peptide. This is evident in the gel retardation and complexation assay where neutralisation of pDNA occurs at a higher N:P ratio of 6, with a maximum complexation efficiency of 70%. In all cases, it is likely that the presence of the cysteine residues (or other uncharged polar hydrophilic amino acids) at each terminal end enhances pDNA condensation.

Each linear peptide produced nanoparticles <150 nm in size with a zeta potential around 30 mV. At higher ratios, increasing amounts of peptide reduces the number of conformations until the pDNA is fully condensed, consistent with the formation of kinetically and/or thermodynamically stable complexes. This process is evident with comparative Peptide 11 where large particles form at lower N:P ratios, but particle size decreases with increased N:P ratio and cationicity. However, the five other peptides studied produced size-suitable nanoparticles immediately from N:P ratio of 1, which is indicative of the strong cationic nature due to inclusion of several arginine and histidine residues. The production of size-suitable cationic particles formed by each peptide with pDNA indicates the potential for cellular delivery of nucleic acids.

Particle size distribution analysis of comparative Peptides 7, 8, 9 and Peptide 10 of the present invention showed PDI between 0.2 and 0.4 indicating size distributions close to homogeneity. The presence of cysteine residues in the peptide sequence may add to the stability of the particles through the formation of disulphide bonds. These bonds have the potential to form between neighbouring peptide chains or within the chain itself, and may serve to strengthen the bonds forming the complexes.

Transfection studies showed lower efficiency in both MCF-7 and MDA-MB-231 cells for all of the linear peptides, with the exception of Peptide 10 (of the present invention). Peptide sequence is a major consideration here and the difference in transfection efficiency highlights the effect of sequence on cell penetrating peptide (CPP) functionality. Comparative Peptides 7 and 8 were designed to have arginine residues at the edges of the peptide chain, flanked by tryptophan residues and histidine residues at the centre. Conversely, comparative Peptide 9 and Peptide 10 of the present invention were designed to have one tryptophan/alanine residue at the centre. Peptide 9 had histidine and arginine residues interleaved along the sequence but Peptide 10 had a series of arginine residues on each side of the central tryptophan/alanine with a series of histidine residues at the edge of the sequence. From the transfection data, it is clear that Peptide 10, with a series of histidine residues at each terminal, flanking a central tryptophan/alanine with, on each each, a series of arginine residues, is best for transfection and this was an unexpected result.

The central tryptophan/alanine flanked by a series of arginine residues in Peptide 10 may enhance transfection ability. It is likely that the central tryptophan/alanine anchors into the cell membrane, working in concert with the flanking series of arginine residues to facilitate the passage of the peptide through the membrane bilayer. The inclusion of hydrophobic tryptophan residues in the peptides may have a significant impact in the functionality when compared to other similar linear peptides consisting exclusively of cysteine, histidine and arginine. The interaction of hydrophobic moieties is reported to enhance compaction of pDNA resulting in self-assembling particle formation. In the case of peptides of the invention, such as Peptide 10, the preferred central tryptophan residue, which is a strongly hydrophobic amino acid due to the aromatic side chain, may provide the hydrophobicity required for enhanced complex formation and interaction with cell membranes.

A series of Histidine residues were incorporated into each sequence to facilitate endosomal escape and investigate if sequence position affected functionality. Significant increases in transfection were observed following addition of chloroquine with all peptides in MDA-MB-231 cells. However, no difference in transfection was observed with Peptide 10 in MCF-7 indicating this peptide sequence must have at least partial endosomal escape ability. It seems from this result that histidine position in the peptide sequence has an effect on endosomal escape functionality. Histidine positioned at the centre and interleaved throughout the sequence, as with comparative Peptides 7, 8 and 9, renders the escape capabilities of histidine useless. Very low transfection with comparative Peptides 11 and 12, regardless of chloroquine, indicates another rate limiting step is hindering transfection; most likely cellular uptake is not occurring. Endosomal escape was not expected with comparative Peptide 11 which contains no histidine residues. The replacement of two histidine residues with glutamic acid did not enhance endosomal escape in comparative Peptide 12. Glutamic acid is credited as responsible for fusogenic activity in various peptides but inclusion in comparative Peptide 12 resulted only in reducing the overall cationicity of the peptide and reducing the proton sponge potential of histidine. In the case of Peptide 10 of the present invention, some endosomal escape activity is observed indicating that histidine positioned at each terminus is functional.

So far, Peptide 10 of the present invention has shown the most promise in initial studies; condensing and packaging pDNA into nanoparticles suitable for intracellular delivery. The transfection efficiencies produced with Peptide 10 of the present invention in two breast cancer cell lines were impressive and investigation into endosomal escape capability was encouraging. With this evidence combined, it was decided that Peptide 10 of the present invention would be taken forward for further characterisation.

Confocal microscopy confirmed that Peptide 10 of the present invention delivered Cy3 labelled pDNA intracellularly to MDA-MB-231 and intra-nuclear DNA was detected with orthoganol sectioning. It must be noted that a large proportion of Cy3-pDNA can be visualised in the cytosol, even 4 h post-transfection. Given the evidence of only partial endosomal escape in MDA-MB-231 cells in the chloroquine study, it is likely this Cy3-pDNA is trapped in endosomes; prevented from progressing to the nucleus. Again, modification of Peptide 10 with increased histidine residues may help to overcome this problem. This was not the case in MCF-7 cells and highlights the difference between the cell lines tested. The dominant endocytic processes in MDA-MB-231 cells are therefore heavily involved in the cellular uptake patterns of Peptide 10 of the present invention. Additionally, with regards to endosomal escape, it is probable that the robust endocytic routes in the metastatic MDA-MB-231 cells produce better quality endosomes which are more difficult to escape than in MCF-7 cells. Nevertheless, impressive transfection efficiency with Peptide 10 of the present invention was observed in a further two cell lines, namely DU145 and PC-3 prostate cancer cells, indicating that Peptide 10 of the present invention is versatile and has potential for delivery to a range of cell lines.

Cell viability studies in both breast and prostate cancer cell lines revealed that Peptide 10 of the present invention caused weak toxicity, if any, even at a high N:P ratio of 20. This highlights the innocuous nature of Peptide 10 of the present invention. The lack of toxicity observed with Peptide of the present invention is important because gene therapeutics have the potential to circumvent the problematic side effects with conventional cancer treatments, however this would be fruitless if the delivery vehicle then caused toxicity.

So far, favourable transfection efficiency and lack of cytotoxicity in vitro suggest that Peptide 10 of the present invention has potential to be a successful gene delivery agent. However, promising in vitro results do not always translate in the in vivo setting, and it was decided that a small study investigating the activity of Peptide 10 of the present invention in vivo was warranted. Peptide 10/pLuc complexes were delivered via tail vein injection to BALB/c SCID mice bearing MDA-MB-231 xenografts to investigate if the complexes would be functional in vivo and where, in the body, luminescence might be detected. It is well established that cationic delivery systems are rapidly detected and cleared by RES/MPS, via opsonisation and phagocytosis. Cationic vectors are particularly susceptible to interaction with anionic serum proteins; triggering the initial opsonisation process. A 10-fold increase in luciferase expression in the lungs, liver and kidney is indicative that Peptide 10/pLuc particles have been recognised and cleared to MPS organs for destruction. The luciferase detected in such organs is a result of local cells being transfected, and in addition to the 5-fold increase in gene expression detected in the tumour confirms the complexes are functional in vivo. This is extremely encouraging because it indicates that Peptide 10 of the present invention has the ability to package and protect genetic material in complex physiological conditions before facilitating successful transfection.

With respect to wound healing studies, it was shown that successful transfection was observed for Peptide 10/pEGFP-N1 complexes, ranging from N:P ratio of 6 to 20 in NCTC-929, HMEC-1 and, HaCaT cell lines. The optimal N:P ratio for NCTC-929, HMEC-1, and HaCaT cells was found to be N:P 10 (24.82%), 6 (19.19%) and 8 (41.73%) respectively. Cell viability studies revealed that Peptide 10 of the present invention caused weak toxicity in the NCTC-929 and HaCaT cell lines at N:P ratios of 15 and 20. However, no cytotoxic effects were observed for the HMEC-1 cells irrespective of the N:P ratio. These results further emphasise the innocuous nature of Peptide 10 of the present invention.

Analysis of miR-31 upregulation via qRT-PCR showed that there was a significant upregulation in its expression NCTC-929, HMEC-1, and HaCaT cells. Up-regulation of miR-31 in NCTC-929 cells helps to explain the increase in cell migration at the 48 h time points as analysed by the wound scratch assay. It was shown that, compared to the untreated control, there was a significant (**, $p<0.01$) fold change in remaining wound area in the Peptide 10/pmiR-31 group compared to the untreated control. In HMEC-1 cells miR-31 upregulation translated to an increase in cell migration (*, $p<0.05$) at the 48 h time point. The tubule formation assay shows that, at the 48 h time point, there is a significant increase in both total tubule number and branching points. This increase in total tubule length and branching points in the Peptide 10/pmiR-31 group was sustained at the 72 h time point, but not significantly. These results demonstrate that miR-31 upregulation has pro-angiogenic properties. Upregulation of miR-31 in HaCaT cells showed a significant (, $p<0.01$) increase in cell migration at the 24 h, 48 h, and 72 h. A significant (, $p<0.01$) increase in cell migration was also observed in the Peptide 10/pEGFP-N1 group at the 24 h time point. These are exceedingly promising results, as it further shows that Peptide 10 of the present invention can transfect a range of cell times related to the skin, and also induce functional effects via the delivered cargo.

Furthermore, it was established that loading of Peptide 10/pEGFP-N1 nanoparticles was successfully achieved post-electrospinning, and no damage to the integrity was evident from the gel electrophoresis image. The release profile showed that 100% of all loaded cargo was released over a 48 h period. Furthermore, the particles were found to retain functionality as exhibited via the transfection study in NCTC-929 cells. After in vivo testing, it was evident that the nanoparticle (NP) system enhanced keratinocyte proliferation and migration as shown through significant increases in epidermal (*, $p<0.05$) and stratum corneum (***, $p<0.001$) thickness. This is extremely encouraging because it indicates that Peptide 10/pmiR-31 loaded nanofibres can efficiently deliver the nanoparticles in vivo and result in significant effects, forming the bases of a new wound healing device.

The versatility of Peptide 10 of the present invention in transfecting a range of cell lines to produce transfection efficiency coupled with the lack of toxicity observed, classes this linear peptide as a promising gene delivery agent. Additionally, Peptide 10 of the present invention has shown functionality delivering miR31 for wound healing applications in a PVA electrospun patch. The process of designing a number of variant peptides, and characterisation of each to determine the optimal peptide sequence for functionality has resulted in the discovery of a novel peptide for gene delivery.

REFERENCES

1. Scheller A, Oehlke J, Wiesner B, Dathe M, Krause E, Beyermann M, et al. Structural requirements for cellular uptake of alpha-helical amphipathic peptides. J Pept Sci. 1999; 5:185-94.
2. Mitchell D J, Kim D T, Steinman L, Fathman C G, Rothbard J B. Polyarginine enters cells more efficiently than other polycationic homopolymers. J Pept Res. 2000; 56:318-25.
3. Wender P A, Mitchell D J, Pattabiraman K, Pelkey E T, Steinman L, Rothbard J B. The design, synthesis, and evaluation of molecules that enable or enhance cellular uptake: peptoid molecular transporters. Proc Natl Acad Sci USA. 2000; 97(24):13003-8.
4. Cahill K. Molecular electroporation and the transduction of oligoarginines. Phys Biol. 2009; 7:16001.
5. Melikov K, Chernomordik L V. Arginine-rich cell penetrating peptides: from endosomal uptake to nuclear delivery. Cell Mol Life Sci. 2005; 62(23):2739-49.
6. Mason A J, Leborgne C, Moulay G, Martinez A, Danos 0, Bechinger B, et al. Optimising histidine rich peptides for efficient DNA delivery in the presence of serum. J Control Release. 2007; 118(1):95-104.
7. Lo S L, Wang S. An endosomolytic Tat peptide produced by incorporation of histidine and cysteine residues as a nonviral vector for DNA transfection. Biomaterials. 2008 May; 29(15):2408-14.
8. Mann A, Shukla V, Khanduri R. Linear short histidine and cysteine modified arginine peptides constitute a potential class of DNA delivery agents. Mol Pharm. 2014; 11(3): 683-96.
9. Bauhuber S, Hozsa C, Breunig M, Gopferich A. Delivery of nucleic acids via disulfide-based carrier systems. Adv Mater. 2009; 21(32-33):3286-306.
10. Lushchak V. Glutathione Homeostasis and functions: potential targets for medical interventions. J Amino Acids. 2011; 2012.
11. Sharma R, Nisakar D, Shivpuri S, Ganguli M. Contrasting effects of cysteine modification on the transfection efficiency of amphipathic peptides. Biomaterials. 2014; 35:6563-75.
12. Tanaka K, Anazawa T K, Gawa T O, Uda Y S, Akashima Y T, Ukuda T F, et al. A Novel, Bio-Reducible Gene Vector Containing Arginine and Histidine Enhances Gene Transfection and Expression of Plasmid DNA. Chem Pharm Bull. 2011; 59(2):202-7.
13. McKenzie D L, Smiley E, Kwok K Y, Rice K G. Low Molecular Weight Disulfide Cross-Linking Peptides as Nonviral Gene Delivery Carriers. Bioconjug Chem [Internet]. 2000 November; 11(6):901-9. Available from: ≤http://pubs.acs.org/doi/abs/10.1021/bc000056i≥
14. Klein P M, Maller K, Troiber C, Kos P, Levacic A K, Edinger D, et al. Twin disulfides as opportunity for improving stability and transfection efficiency of oligoaminoethane polyplexes. J Control Release. 2014; (10.1016/j.jconrel.2014.12.035).
15. Bode S a, Wallbrecher R, Brock R, van Hest J C M, Löwik DWPM. Activation of cell-penetrating peptides by disulfide bridge formation of truncated precursors. Chem Commun (Camb). 2014; 50(4):415-7.
16. Guterstam P, Madani F, Hirose H, Takeuchi T, Futaki S, El Andaloussi S, et al. Elucidating cell-penetrating peptide mechanisms of action for membrane interaction, cellular uptake, and translocation utilizing the hydrophobic counter-anion pyrenebutyrate. Biochim Biophys Acta. 2009; 1788(12):2509-17.

The invention claimed is:

1. A peptide comprising X-$(Xaa_1)_a$-$(Xaa2)_b$-Y-$(Xaa3)_c$-$(Xaa4)_d$-Z, or a salt or amide thereof, wherein:
   each of X and Z is independently selected from Asn, Cys, Gln, Gly, Ser, Thr and Tyr;
   one of $Xaa_1$ and $Xaa_2$ is His and the other of $Xaa_1$ and $Xaa_2$ is Arg;
   one of $Xaa_3$ and $Xaa_4$ is His and the other of $Xaa_3$ and $Xaa_4$ is Arg;
   the amino functional group of X is optionally acylated;
   the carboxylate functional group of Z is optionally amidated;
   Y is selected from Ala and Trp;
   each of a and d is independently an integer from 2 to 4; and
   each of b and c is independently an integer from 2 to 4.

2. The peptide according to claim 1, wherein each of $Xaa_2$ and Xaa3 is Arg.

3. The peptide according to claim 1, wherein each of $Xaa_1$ and Xaa4 is His.

4. The peptide according to claim 1, wherein each of a and d is identical and is 2 to 4.

5. The peptide according to claim 4, wherein each of a and d is 3.

6. The peptide according to claim 1, wherein each of b and c is identical and is 2 to 4.

7. The peptide according to claim 6, wherein each of b and c is 3.

8. The peptide according to claim 1, wherein each of a, b, c and d is 3.

9. The peptide according to claim 1, wherein each of X and Z is identical and selected from Asn, Cys, Gln, Gly, Ser, Thr and Tyr.

10. The peptide according to claim 1, wherein each of X and Z is Cys.

11. The peptide according to claim 1, wherein Y is Trp.

12. The peptide according to claim 1, wherein the sum of b and c is at least six.

13. The peptide according to claim 1, wherein the sum of a and d is at least six.

14. The peptide according to claim 1, wherein each of X and Z is Cys; each of $Xaa_1$ and Xaa4 is His; each of a and d is independently an integer from 2 to 4; each of $Xaa_2$ and Xaa3 is Arg; each of b and c is independently an integer from 2 to 4; and Y is Trp.

15. The peptide according to claim 1, wherein the net positive charge of the peptide is 6 to 8.

16. The peptide according to claim 15, wherein the net positive charge of the peptide is 6.

17. The peptide according to claim 1, wherein the peptide is CHHHHRRRWRRRHHHC (SEQ ID NO: 4).

18. The peptide according to claim 1, wherein the peptide is 11-20 amino acids in length.

19. A method of delivering an anionic cargo into a cell, wherein the method comprises contacting the cell with a composition comprising a peptide and the anionic cargo, and wherein the peptide consists of the amino acid sequence X-$(Xaa_1)_a$-$(Xaa2)_b$-Y-$(Xaa3)_c$-$(Xaa4)_d$-Z, or a salt thereof, wherein:
   each of X and Z is independently selected from the group consisting of Asn, Cys, Gln, Gly, Ser, Thr and Tyr;
   one of $Xaa_1$ and Xaa2 is His and the other of $Xaa_1$ and Xaa2 is Arg;
   one of Xaa3 and Xaa4 is His and the other of Xaa3 and Xaa4 is Arg;
   the amino functional group of X is optionally acylated;
   the carboxylate functional group of Z is optionally amidated;
   Y is selected from Ala or Trp;
   each of a and d is independently an integer from 2 to 4; and
   each of b and c is independently an integer from 2 to 4.

20. A gene therapy method comprising administering to a subject in need thereof a composition comprising a peptide and a therapeutic nucleic acid, and wherein the peptide consists of the amino acid sequence X-$(Xaa_1)_a$-$(Xaa2)_b$-Y-$(Xaa3)_c$-$(Xaa4)_d$-Z, or a salt thereof, wherein:
   each of X and Z is independently selected from the group consisting of Asn, Cys, Gln, Gly, Ser, Thr and Tyr;
   one of $Xaa_1$ and Xaa2 is His and the other of $Xaa_1$ and Xaa2 is Arg;
   one of Xaa3 and Xaa4 is His and the other of Xaa3 and Xaa4 is Arg;
   the amino functional group of X is optionally acylated;
   the carboxylate functional group of Z is optionally amidated;
   Y is selected from Ala or Trp;
   each of a and d is independently an integer from 2 to 4; and
   each of b and c is independently an integer from 2 to 4.

21. The method of claim 20, wherein the method is for treating infection, cancer, or a wound.

22. The method of claim 21, wherein the cancer is selected from the group consisting of breast cancer, prostate cancer, brain cancer, lung cancer, pancreatic cancer, ovarian cancer and skin cancer.

* * * * *

UNITED STATES PATENT AND TRADEMARK OFFICE
CERTIFICATE OF CORRECTION

PATENT NO. : 12,049,519 B2  
APPLICATION NO. : 17/437025  
DATED : July 30, 2024  
INVENTOR(S) : McCarthy et al.

Page 1 of 1

It is certified that error appears in the above-identified patent and that said Letters Patent is hereby corrected as shown below:

In the Claims

Column 44, at Line 24, in Claim 17, "CHHHHRRRWRRRHHHC (SEQ ID NO: 4)" should read: --CHHHRRRWRRRHHHC (SEQ ID NO: 4)--.

Signed and Sealed this  
Twenty-ninth Day of April, 2025

Coke Morgan Stewart  
*Acting Director of the United States Patent and Trademark Office*